US007944478B2

(12) United States Patent
Shiibashi et al.

(10) Patent No.: US 7,944,478 B2
(45) Date of Patent: May 17, 2011

(54) MEDICAL IMAGE PHOTOGRAPHING SYSTEM AND MEDICAL IMAGE MANAGING METHOD

(75) Inventors: Takao Shiibashi, Hachioji (JP); Naoto Moriyama, Hachioji (JP); Wataru Motoki, Hachioji (JP)

(73) Assignee: Konica Minolta Holdings, Inc., Tokyo (JP)

( * ) Notice: Subject to any disclaimer, the term of this patent is extended or adjusted under 35 U.S.C. 154(b) by 2199 days.

(21) Appl. No.: 10/797,352

(22) Filed: Mar. 9, 2004

(65) Prior Publication Data
US 2004/0190780 A1  Sep. 30, 2004

(30) Foreign Application Priority Data

Mar. 28, 2003  (JP) ................. 2003-091042

(51) Int. Cl.
*H04N 5/232* (2006.01)
(52) U.S. Cl. .............. 348/211.2; 348/222.1; 348/333.02
(58) Field of Classification Search ............... 348/207.1, 348/211.2, 222.1, 231.99, 231.3, 333.01, 348/333.02; 382/128–132, 305
See application file for complete search history.

(56) References Cited

U.S. PATENT DOCUMENTS

| | | | |
|---|---|---|---|
| 5,757,021 A | 5/1998 | Dewaele | |
| 6,348,793 B1 | 2/2002 | Balloni et al. | |
| 6,409,660 B1 | 6/2002 | Sjöqvist | |
| 6,433,341 B1 | 8/2002 | Shoji | |
| 6,859,513 B2 | 2/2005 | Sako | |
| 6,954,767 B1* | 10/2005 | Kanada | 382/131 |
| 2001/0041991 A1* | 11/2001 | Segal et al. | 705/3 |
| 2002/0048222 A1 | 4/2002 | Wright et al. | |
| 2002/0085026 A1 | 7/2002 | Bacionek et al. | |
| 2002/0091659 A1* | 7/2002 | Beaulieu et al. | 706/62 |
| 2002/0113590 A1 | 8/2002 | Haworth et al. | |
| 2002/0188187 A1* | 12/2002 | Jordan | 382/128 |
| 2003/0020813 A1* | 1/2003 | Iida | 348/207.1 |
| 2004/0071263 A1* | 4/2004 | Motoki | 378/98 |

FOREIGN PATENT DOCUMENTS

EP  1 217 569 A2  6/2002
(Continued)

OTHER PUBLICATIONS

Japanese Office Action dated Sep. 29, 2009 and English translation thereof issued in a counterpart Japanese Application No. 2004-024166.

*Primary Examiner* — Gevell Selby
(74) *Attorney, Agent, or Firm* — Holtz, Holtz, Goodman & Chick, PC

(57) ABSTRACT

A medical image photographing system comprising a control apparatus for corresponding a photographing order information related to medical photography and a medical image and managing them, and a portable terminal for obtaining the photographing order information from the control apparatus; wherein the control apparatus has a first communication unit for communicating with the portable terminal, and a first control unit for transmitting the photographing order information through the first communication unit to the portable terminal; and the portable terminal has a second communication unit for communicating with the control apparatus, a display unit for displaying a display information, and a second control unit for receiving the photographing order information from the control apparatus through the second communication unit, extracting the photographing order information corresponding to a predetermined extract condition from a received photographing order information, and displaying a extracted photographing order information on the display unit.

4 Claims, 19 Drawing Sheets

FOREIGN PATENT DOCUMENTS

| | | |
|---|---|---|
| JP | 8-289884 A | 11/1996 |
| JP | 2000-139888 A | 5/2000 |
| JP | 2000-217807 A | 8/2000 |
| JP | 2002-125960 A | 5/2002 |
| JP | 2002-133394 A | 5/2002 |
| JP | 2002-200062 A | 7/2002 |
| JP | 2002-200063 A | 7/2002 |
| JP | 2003-210445 A | 7/2003 |
| JP | 2003-210446 A | 7/2003 |

\* cited by examiner

| PHOTOGRAPHING ID | PATIENT ID | NAME | SEX | AGE | HOSPITAL ROOM | REQUESTING DEPARTMENT | PHOTOGRAPHIC PART | PHOTOGRAPH NUMBER | PHOTOGRAPH SIZE | OPERATOR ID | CASSETTE ID | RADIOGRAPHING APPARATUS ID |
|---|---|---|---|---|---|---|---|---|---|---|---|---|
| 20020101001 | 10000002 | ○○○○ | MAN | 40 | 201 | SURGERY | SKULL A→D | 3 | 11x14 | | | |
| 20020101002 | 10000002 | ○○○○ | MAN | 40 | 201 | SURGERY | SKULL P→A | 3 | 11x14 | | | |
| 20020101003 | 10000002 | ○○○○ | MAN | 40 | 201 | SURGERY | CHEST P→A | 4 | 14x17 | | | |
| 20020101004 | 10000002 | ○○○○ | MAN | 40 | 201 | SURGERY | CHEST R→L | 4 | 14x17 | | | |
| 20020101005 | 10000005 | △△△△ | WOMAN | 50 | 205 | INTERNAL MAEDICINE | ABDOMEN LAT | 5 | 14x17 | | | |
| 20020101006 | 10000005 | △△△△ | WOMAN | 50 | 205 | INTERNAL MAEDICINE | ABDOMEN P→A | 5 | 14x17 | | | |
| ... | ... | ... | ... | ... | ... | ... | ... | ... | ... | ... | ... | ... |

| PHOTOGRAPHING ID | PHOTOGRAPHING DATE | OPERATOR ID | CASSETTE ID | RADIOGRAPHING APPARATUS ID | READING APPARATUS ID | ERROR FLAG |
|---|---|---|---|---|---|---|
| 20020101001 | 2003/3/3 | sato1234 | 0400010802201 6 | A101010 | E1100101 | |
| 20020101002 | 2003/3/3 | tanaka2513 | 1010076010010 0 | A221101 | F1210012 | V |
| 20020101003 | 2003/3/4 | suzuki777 | 0400044483394 0 | B001001 | H3302009 | |
| ... | ... | ... | ... | ... | ... | ... |

| OPERATOR:TARO SUZUKI | CONDITION | | | | RESERVATION 2 CASE | SUSPEND 0 CASE |
|---|---|---|---|---|---|---|
| AllPdaDBdelete | | | | | | |

| PATIENT ID | -TAB TYPE | NAME | SEX | BIRTH DATE | RADIOGRAPHIC PART | PHOTOGRAPH NUMBER | SUSPEND |
|---|---|---|---|---|---|---|---|
| 0001 | → | ICHIRO YAMADA | MALE | / / | CHEST ETC OBLIQUE | 0/2 | SUSPEND |
| 12345 | | TARO SAKURA | MALE | / / | INFANT CHEST-PA | 0/2 | SUSPEND |

ALL SELECTION

△△ △ ▽ ▽▽

TRANSMIT    RECEIVE

| NEW/RETRIEVAL | MODIFY | DELETE | SET CONDITION | EXTRACT CONDITION | UPDATE LIST | CONFIRMATION SCREEN |

| OPERATOR: | | |
|---|---|---|
| PATIENT ID | 12345 | |
| NAME ROMAN LETTER | sakura tarou | |
| NAME KANA | サクラ タロウ | |
| NAME KANJI | 桜 大郎 | |

| SEX | MALE |
|---|---|
| BIRTH DATE (AGE) | 1970-04-23 O CLOCK MINUTE SECOND (32 YEARS 10 MONTHS OLD) |
| BIRTH DATE (TIME UNSHOWN) | 1970-04-23 (32 YEARS 10 MONTHS OLD) |
| PATIENT COMMENT | |

1/4  ◁ ▷  (RETRIEVAL)

ABC/abc | keyboard | kana a b c d e f g _ @ DEL BS
h i j k l m n " ↑
o p q r s t u ' ↓
v w x y z # & , ; ENTER
Caps Lock [Space]

ALL CLEAR | CANCEL
(OK)

| PHOTOGRAPHIC PART | UNREGISTERED | REGISTERED | TOTAL |
|---|---|---|---|
| CHEST-CHEST DECUBITUS | 10CASE | 2CASE | 12CASE |
| ... | | | |
| ... | | | |
| ... | | | |

RESERVATION [ ] CASE    REGISTRATION [ ] CASE

← [ 1/ ] →

[ CANCE ]  [ OK ]

FIG.13A

| PATIENT ID | NAME (KANJI) | HOSPITAL WARD |
|---|---|---|
| 0001 | ICHIRO YAMADA | |
| 12345 | TARO SAKURA | |

0/2  ALL

PATIENT ID 0001   ICHIRO YAMADA
SEX M   AGE
HOSPITAL WARD   HOSPITAL ROOM

01/02

CHEST ETC OBLIQUE 11×14  3
0400010802016
suzuki777
A101010

CANCEL  OK

*132*

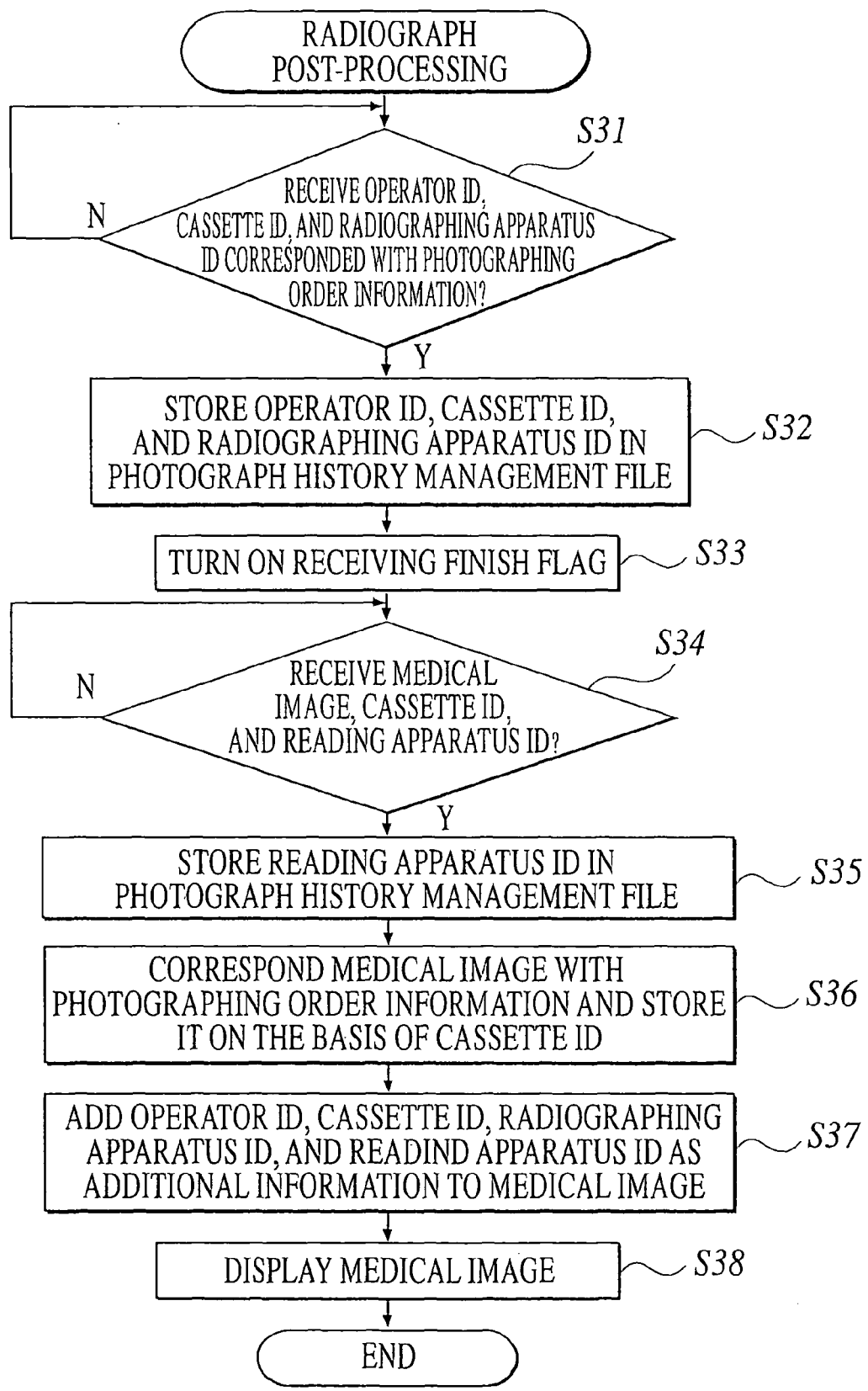

FIG.15

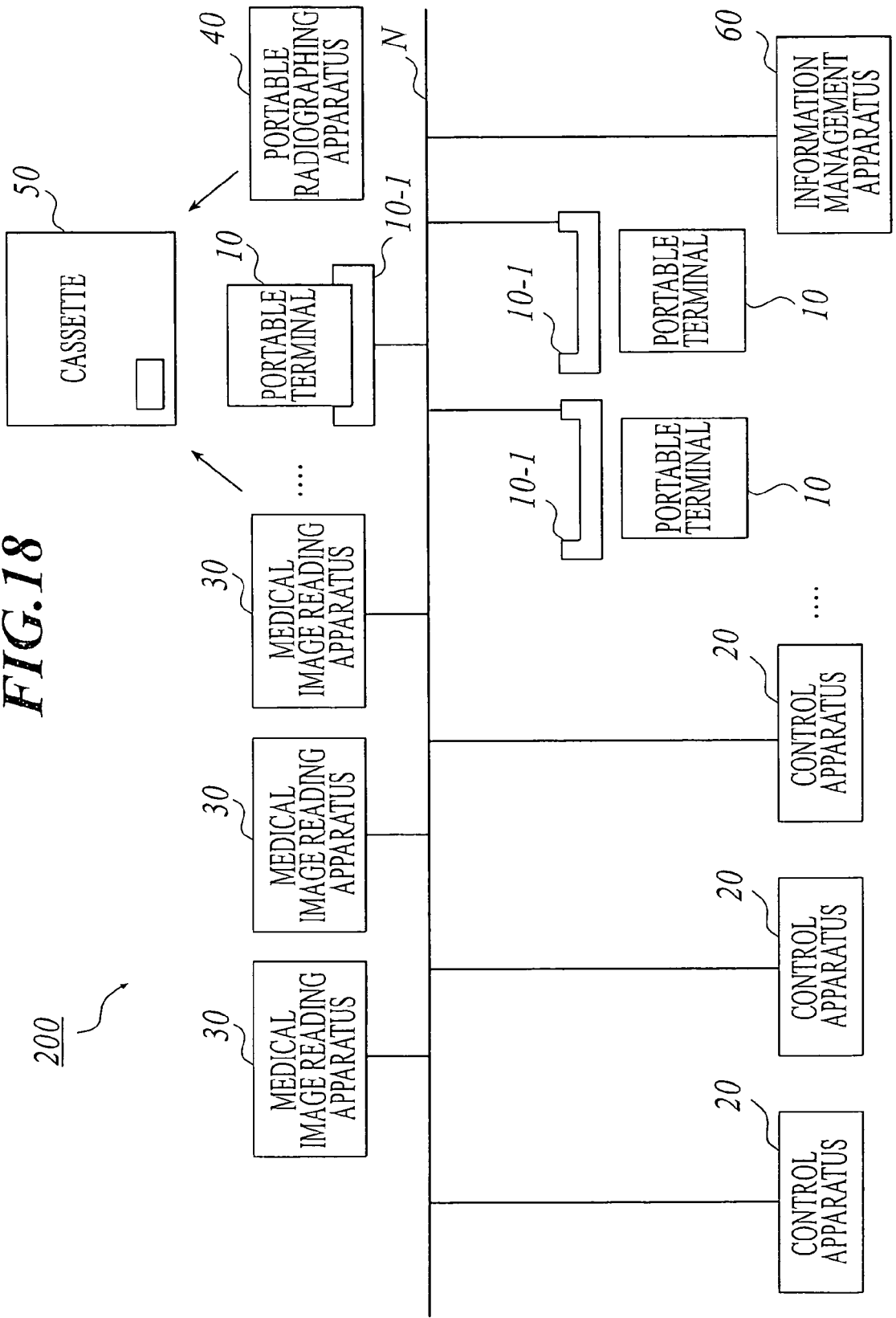

MEDICAL IMAGE PHOTOGRAPHING SYSTEM AND MEDICAL IMAGE MANAGING METHOD

FIELD OF THE INVENTION

The present invention relates to medical image photographing system and medical image managing method.

DESCRIPTION OF THE RELATED ART

In a medical field, there has been utilized a medical image photographing system having, for example, a computed tomography apparatus (hereinafter referred to as "CT" (Computed Tomography)), a computed radiography apparatus (hereinafter referred to as "CR" (Computed Radiography)), a magnetic resonance radiographing apparatus (hereinafter referred to as "MRI" (Magnetic Resonance Imaging)) or the like. This medical image photographing system is a system for photographing a subject, and obtaining medical image as a digital image data.

Of these radiographing apparatuses, a radiographing apparatus uses a medical image conversion panel having a photostimulable phosphor formed on a support member thereof, and thereby the radiation ray penetrating through a subject is assimilated in the photostimulable phosphor of this conversion panel and the radiation energy is accumulated corresponding to the quantity of radiation transmitted through each part of a subject. After that, the radiation energy stored by scanning this phosphor with irradiation of excitation light such as infrared rays is emitted as fluorescence, the fluorescence thereof is photoelectrically converted, and thus the medical image signal is obtained. The medical image obtained as above is output to the output apparatus such as film or CRT after image processing is executed thereto. Thereby, the medical image is visualized or the like, stored together with the patient information in the filing apparatus such as a server, and utilized for medical activities.

Two system structures are usually applied to the medical image photographing system utilizing such a radiographing apparatus. One of them is a medical image photographing system of an earlier development for imaging in a radiographing room by disposing in the radiographing room or in the vicinity of the radiographing room an apparatus for carrying out radiography and reading an image and a photostimulable phosphor plate. This system can carry out radiography and read an image at the same time in the radiographing room.

The other is a medical image photographing system for carrying out radiography in a doctor's round visits by utilizing a portable X-ray radiographing apparatus (transportable X-ray source) capable of being transported with the doctor's round visits to patients incapable of being imaged in the radiographing room such as the patient who is suffering from bone fracture, cerebrovascular or the like and the patient who is on being managed in ICU, and a portable cassette housing a phosphor plate (for example, refer to JP-Tokukai 2000-139888). In this system, the cassette is inserted to a reading apparatus for the cassette after imaging, and the image is read.

Further, there has been considered the structure in which the additional information is added to the image data imaged by an image data output apparatus of the medical image photographing system so as to be output in an image forming apparatus such as printer (for example, refer to JP-tokukai 2002-133394).

However, when it comes to moving to carry out a X-ray photography, a plurality of operators and a plurality of hospital wards and hospital rooms unusually hamper a certain operator trying to extract from the database of server a necessary information for his imaging work. In this case, there is the possibility that the imaging works including the preparation of the cassette corresponding to the patient to be imaged and the imaging for the patient may take a long time.

SUMMARY OF THE INVENTION

The object of the present invention is to make more effective the photography when it comes to moving to photograph a medical image.

In order to solve the above-described problems, in accordance with the first aspect of the present invention, a medical image photographing system comprises a control apparatus for corresponding a photographing order information related to medical photography and a medical image and managing them, and a portable terminal for obtaining the photographing order information from the control apparatus;

wherein the control apparatus has a first communication unit for communicating with the portable terminal, and a first control unit for transmitting the photographing order information through the first communication unit to the portable terminal; and the portable terminal has a second communication unit for communicating with the control apparatus, a display unit for displaying a display information, and a second control unit for receiving the photographing order information from the control apparatus through the second communication unit, extracting the photographing order information corresponding to a predetermined extract condition from a received photographing order information, and displaying a extracted photographing order information on the display unit.

According to the first aspect of the present invention, the portable terminal extracts the photographing order information on the basis of the predetermined extract condition and displays the extracted photographing order information. Therefore, the photographer for patient can make more effective the photography because he can photograph a patient on the basis of the photographing order information corresponding to the extract condition.

It is preferable that the second control unit computes an additional information having one of or both of a size and the number of cassette from the photographing order information to be extracted, and displays the additional information and the photographing order information on the display unit.

According to this structure, the portable terminal displays one of or both of a size and the number of cassette necessary for the imaging corresponding to the photographing order information to be extracted on the basis of the predetermined extract condition. Therefore, the photographer for patient can make much more effective the photography because he can easily and securely prepare the cassette with reference to one of or both of a size and the number of cassette corresponding to the extract condition.

Further, in accordance with the second aspect of the present invention, a medical image photographing system comprises a control apparatus for corresponding a photographing order information related to medical photography and a medical image and managing them, and a portable terminal for obtaining the photographing order information from the control apparatus, further comprising:

a extracting unit for extracting a predetermined data from the photographing order information to be sent to the portable terminal; and a display unit for displaying a extract result of the extracting.

According to this structure, the predetermined data is extracted from the photographing order information to be transmitted to the portable terminal and the extract result is displayed. Therefore, the photographer for patient can make more effective the photography because he can photograph a patient on the basis of the extract result.

It is preferable that the data to be extracted has one of or both of a size and the number of cassette necessary for imaging.

According to this structure, the predetermined data is extracted from the photographing order information to be transmitted to the portable terminal and the extract result is displayed. Therefore, the photographer for patient can make more effective the photography because he can photograph a patient on the basis of the extract result.

Further, the portable terminal may have the extracting unit and the display unit.

According to this structure, the portable terminal can extract the predetermined data and display the extract result.

Further, the control apparatus may have the extracting unit and the display unit.

According to this structure, the control apparatus can extract the predetermined data and display the extract result.

Further, the control apparatus may have the extracting unit and the display unit, and the portable terminal may have a display unit and display the extract result of the extracting unit on the display unit.

According to this structure, the extract result extracted by the extracting unit can be displayed on the control apparatus and the portable terminal.

Further, in accordance with the third aspect of the present invention, a medical image managing method in a medical image photographing system comprises a control apparatus for corresponding a photographing order information related to medical photography and a medical image and managing them, and a portable terminal for obtaining the photographing order information from the control apparatus, comprising:

transmitting the photographing order information to the portable terminal in the control apparatus; and receiving the photographing order information from the control apparatus, extracting the photographing order information corresponding to a predetermined extract condition from a received photographing order information, and displaying a extracted photographing order information in the portable terminal.

According to the third aspect of the present invention, the portable terminal extracts the photographing order information on the basis of the predetermined extract condition and displays the extracted photographing order information in the portable terminal. Therefore, the photographer for patient can make much more effective the photography because he can photograph a patient on the basis of the photographing order information corresponding to the extract condition.

It is preferable that the portable terminal computes an additional information having one of or both of a size and the number of cassette necessary for imaging from the photographing order information to be extracted, and displays the additional information and the photographing order information.

According to this structure, the portable terminal computes one of or both of a size and the number of cassette necessary for the imaging corresponding to the photographing order information to be extracted on the basis of the predetermined extract condition, and displays them. Therefore, the photographer for patient can make much more effective the photography because he can easily and securely the cassette with reference to one of or both of a size and the number of cassette corresponding to the extract condition.

Further, in accordance with the fourth aspect of the present invention, a medical image managing method in a medical image photographing system comprising a control apparatus for corresponding a photographing order information related to medical photography and a medical image and managing them, and a portable terminal for obtaining the photographing order information from the control apparatus, comprising:

extracting the photographing order information corresponding to a predetermined extract condition from the photographing order information and displaying a extracted photographing order information in the control apparatus.

According to this structure, the control apparatus extracts the photographing order information on the basis of the predetermined extract condition and displays the extracted photographing order information. Therefore, the photographer for patient can make more effective the photography because he can refer the photographing order information displayed on the control apparatus and corresponding to the extract condition.

It is preferable that the control apparatus transmits the extracted photographing order information to the portable terminal and the portable terminal receives the extracted photographing order information from the control apparatus and displays the extracted photographing order information.

According to this structure, the control apparatus displays the extracted photographing order information and transmits the extracted photographing order information to the portable terminal, and the portable terminal displays the received photographing order information. Therefore, the photographer for patient can make much more effective the photography because he can refer the photographing order information displayed on the control apparatus and corresponding to the extract condition, and photograph a patient by reviewing the photographing order information displayed on the portable terminal.

It is preferable that the control apparatus computes an additional information having one of or both of a size and the number of cassette necessary for imaging from the photographing order information to be extracted, and displays the additional information and the extracted photographing order information.

According to this structure, the control apparatus computes one of or both of a size and the number of cassette necessary for the imaging corresponding to the photographing order information to be extracted on the basis of the predetermined extract condition, and displays one of or both of a size and the number of cassette and the photographing order information. Therefore, the photographer for patient can make much more effective the photography because he can easily and securely prepare the cassette by referring one of or both of a size and the number of cassette displayed on the control apparatus and corresponding to the extract condition.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein;

FIG. 3 is a view showing a data structure of the photographing order information file 161 stored in the storage apparatus 16 of FIG. 2;

FIG. 5 is a view showing a data structure of the photograph history management file stored in the storage apparatus 26 of FIG. 4;

FIG. 8 is a view showing an example of the portable list receiving screen displayed on the display unit 23 of the control apparatus 20;

FIG. 9A is a view showing an example of the input screen on which the patient information displayed to the display unit 23 of the control apparatus 20 is input and FIG. 9B is a view showing an example of the input screen to which the imaging information displayed on the display unit 23 of the control apparatus 20 is input;

FIG. 11 is a view showing an example of the extract result screen of the extracted photographing order information displayed on the display unit 13 of the portable terminal 10;

FIG. 13A is a view showing an example of the patient list screen displayed on the display unit 13 of the portable terminal 10 and FIG. 13B is a view showing an example of the screen displayed on the display unit 13 of the portable terminal 10;

FIG. 14 is a flow chart showing the radiograph post-processing executed by the control apparatus 20;

FIG. 15 is a view showing an example of the portable processing screen displayed on the display unit 23 of the control apparatus 20;

FIG. 18 is a view showing a system structure of the medical image photographing system 200 in the other embodiment applying the present invention.

DETAILED DESCRIPTION OF THE PREFERRED EMBODIMENTS

The first and second embodiments of the present invention will be hereinafter described by turns with reference to the drawings. Here, the scope of the invention is not limited to the drawings. Also, a medical image photographing system for carrying out the photography in a doctor's round visits by utilizing a portable terminal capable of being carried and a transportable radiographing apparatus will be hereinafter described as an example of the characteristic embodiment of the present invention.

First Embodiment

The structure of the first embodiment will be described with reference to FIGS. 1 to 15.

Figure 1:
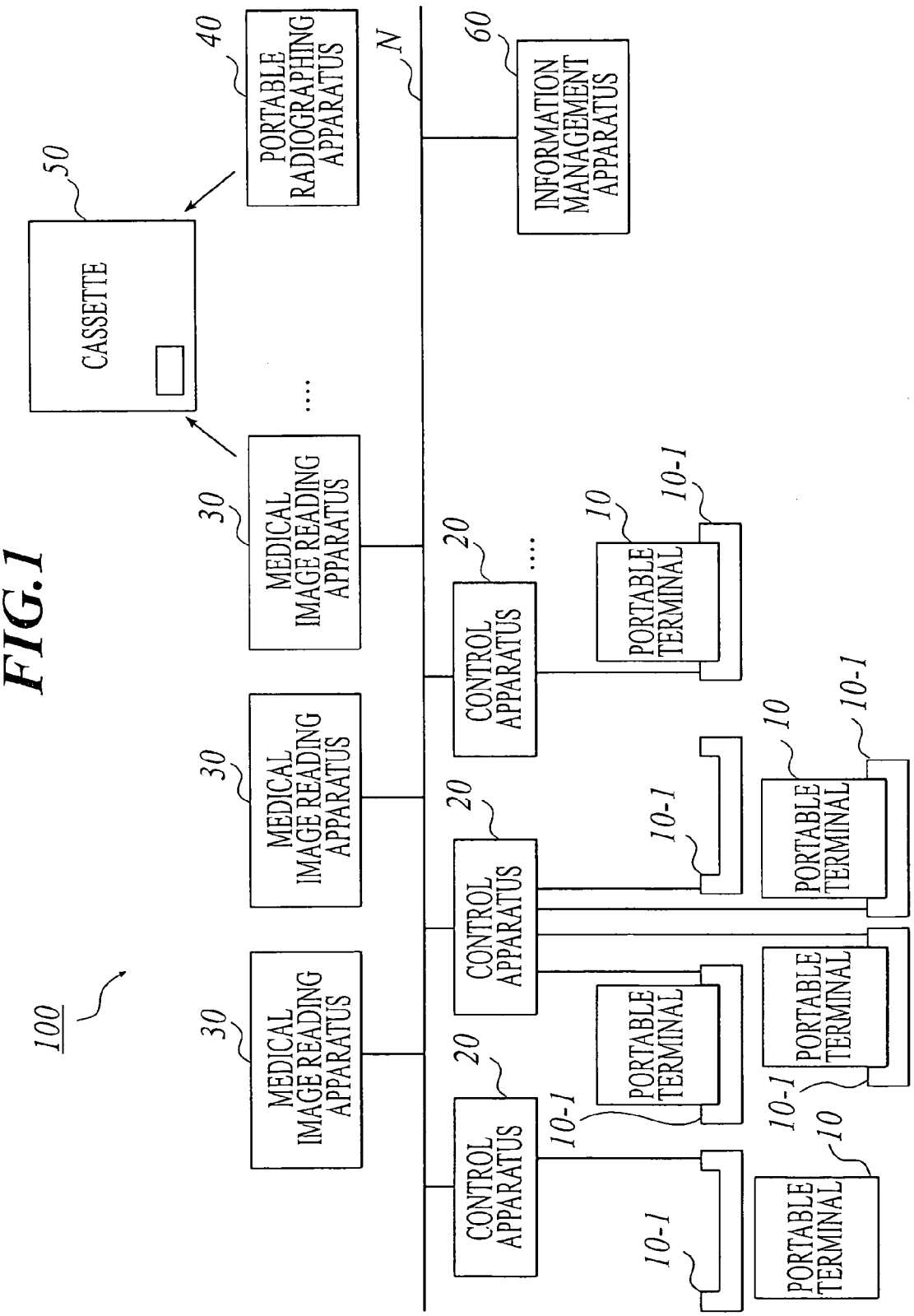
FIG. 1 is a view showing a system structure of the medical image photographing system 100 in the embodiment applying the present invention.

FIG. 1 is a block diagram showing a medical image photographing system 100 of the present invention. As shown in FIG. 1, the medical image photographing system 100 has a portable terminal 10, . . . , a communication terminal 10-1, . . . , a control apparatus 20, . . . , a medical image reading apparatus 30, . . . , a portable radiographing apparatus 40, a cassette 50, and an information management apparatus 60. Further, the control apparatus 20, the medical image reading apparatus 30, and the information management apparatus 60 are connected through a network N. Here, the portable terminal 10, the communication terminal 10-1, the control apparatus 20, and the medical image reading apparatus 30 are respectively disposed at least one. But the number of them is not limited to a certain number.

The portable terminal 10 can be mounted in the communication terminal 10-1. The portable terminal 10 is a portable information terminal apparatus that the operator or the like operating the portable radiographing apparatus 40 carries. The portable terminal 10 communicates with the control apparatus 20 through the communication terminal 10-1. Further, although the portable terminal 10 obtains the photographing order information from the control apparatus 20 and displays the photographing order information, in case the photographing order for patients exists for example, the portable terminal 10 searches the photographing order information corresponding to the preferred patient ID among the photographing order information and displays the photographing order information. Further, the portable terminal 10 obtains the identification information of operator (hereinafter referred to as "operator ID"), the identification information of the cassette 50 (hereinafter referred to as "cassette ID"), and the identification information of the imaging apparatus (hereinafter referred to as "radiographing apparatus ID"), corresponds the operator ID, the cassette ID, and the radiographing apparatus ID with the photographing order information and stores them.

The communication terminal 10-1 is connected with the control apparatus 20 through a cable or the like, and controls transmitting and receiving date between the portable terminal 10 and the control apparatus 20 which are connected with the communication terminal 10-1. For example, the communication terminal 10-1 controls transmitting the photographing order information from the control apparatus 20 to the portable terminal 10, and controls transmitting the operator ID, the cassette ID, and the radiographing apparatus ID from the portable terminal 10 to the control apparatus 20.

The control apparatus 20 receives the photographing order information from the information management apparatus 60, manages the medical image on the basis of the received photographing order information, and manages the photograph history of the medical image on the basis of the information to be received from the portable terminal 10 and the medical image reading apparatus 30. For example, the control apparatus 20 transmits the photographing order information received from the information management apparatus 60 through the communication terminal 10-1 to the portable terminal 10. Further, after the imaging is finished, the control apparatus 20 receives the operator ID, the cassette ID, and the radiographing apparatus ID corresponded to the photographing order information from the portable terminal 10. Further, the control apparatus 20 receives the medical image, the cassette ID corresponded to the medical image, and the identification information of the reading apparatus (hereinafter referred to as "reading apparatus ID"). And the control apparatus 20 corresponds such as the medical image, the operator ID, the cassette ID, the radiographing apparatus ID, and the reading apparatus ID and manages them on the basis of the photographing order information.

The medical image reading apparatus 30 is a medical image reading apparatus for reading the medical image stored in the cassette 50. The medical image reading apparatus 30 irradiates the excited light to the photostimulable phosphor sheet of the cassette 50, thereby photoelectrically converts the photostimulable light irradiated from the sheet, converts analog to digital the obtained image signal, and obtains the medical image. Further, the medical image reading apparatus 30 reads the cassette ID appending to the cassette 50, and corresponds the medical image with the cassette ID and the reading apparatus ID of itself and transmits them to the control apparatus 20.

The portable radiographing apparatus 40 is a transportable source of radiation rays for the medical photography. The portable radiographing apparatus 40 irradiates X-rays to the patient in a doctor's round visits, and stores the medical image in the cassette 50. The cassette 50 houses the photostimulable phosphor sheet storing a part of radiation energy. The portable radiographing apparatus 40 as a source or radiation rays irradiates the radiation rays to the cassette 50. The cassette 50 stores on the photostimulabel phosphor sheet a part of radiation energy passing the subject disposed between the radiation source and the cassette. Here, the barcode or the like storing the cassette ID which is the identification information of the cassette 50 is appended on the surface of the cassette 50.

The information management apparatus 60 manages all photographing order information commanded by the doctor, extracts the photographing order information in accordance with the command requested from the control apparatus 20, and transmits the extracted photographing order information to the control apparatus 20. Here, as another information management apparatus, a receiving apparatus (not shown) for receiving the reservation of the photographing order information may be used, and an information management system such as HIS (Hospital Information System) and RIS (Radiology Information System) may also be used.

The network N is applicable in the various forms of LAN (Local Area Network), WAN (Wide Area Network) and Internet. Here, such as the wireless LAN trouble to the medical equipment of medical institution like hospital is omitted. Although the wireless communication and the infrared communication may be used if possible, considering the important patient information included in the photographing order information is transmitted and received, it is preferable that the photographing order information is encoded.

Next, each apparatus mainly structuring the present invention will be described in details.

Figure 2:
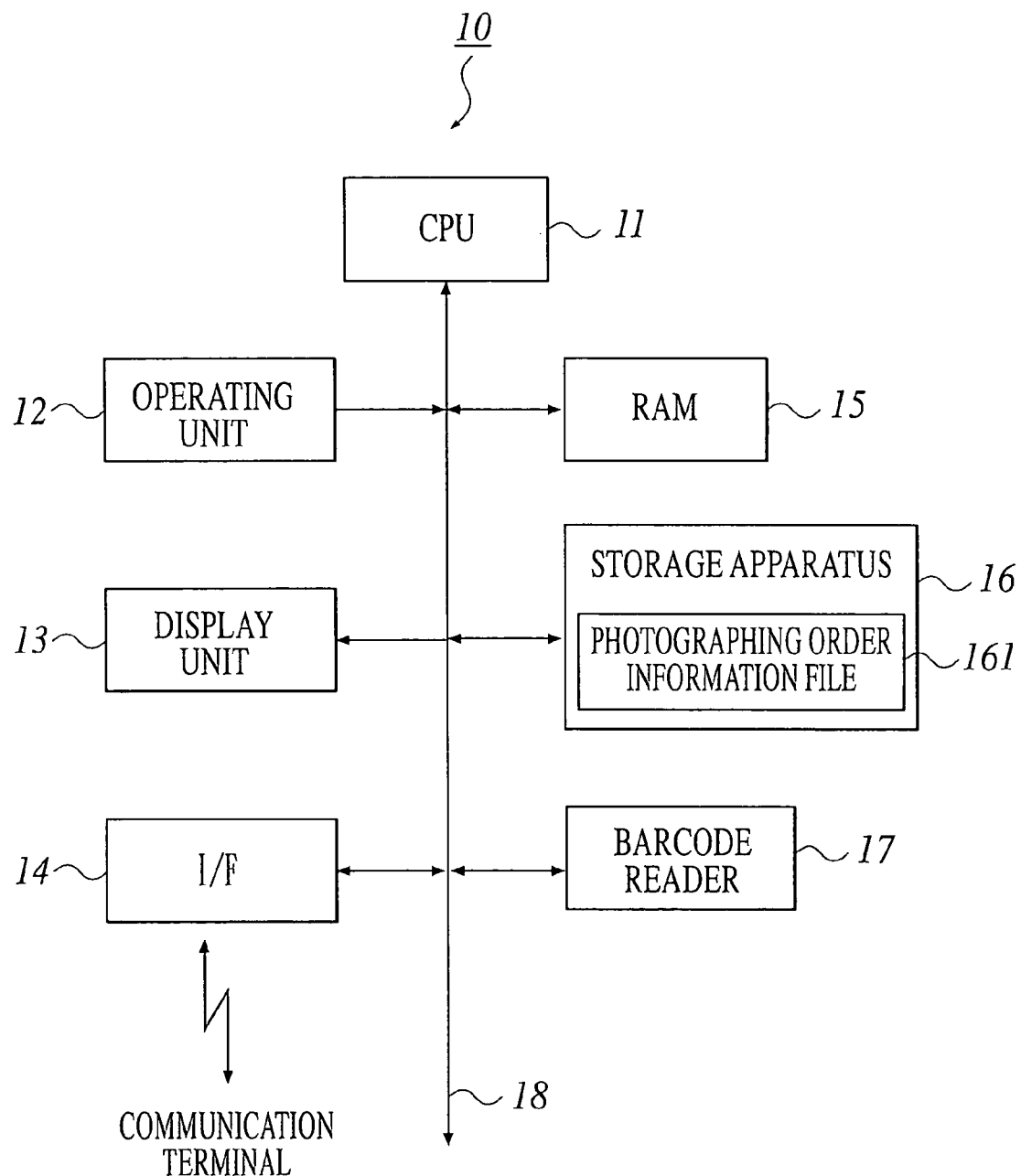
FIG. 2 is a block diagram showing a substantial structure of the portable terminal 10 shown in FIG. 1.

FIG. 2 is a block diagram showing the functional structure of the portable terminal 10. As shown in FIG. 2, the portable terminal 10 has CPU (Central Processing Unit) 11, an operating unit 12, a display unit 13 for displaying and displaying on the portable side, I/F (interface) 14 for communicating, RAM (Random Access Memory) 15, a storage apparatus 16 for storing, and a barcode reader 17. Each unit is connected by a bus 18.

CPU 11 extracts to RAM 15 the program designated out of the system programs and various application programs stored in the storage apparatus 16, and carries out as a control unit the central control for each unit of the portable terminal 10 by cooperating with the program extracted on RAM 15.

Figure 10:
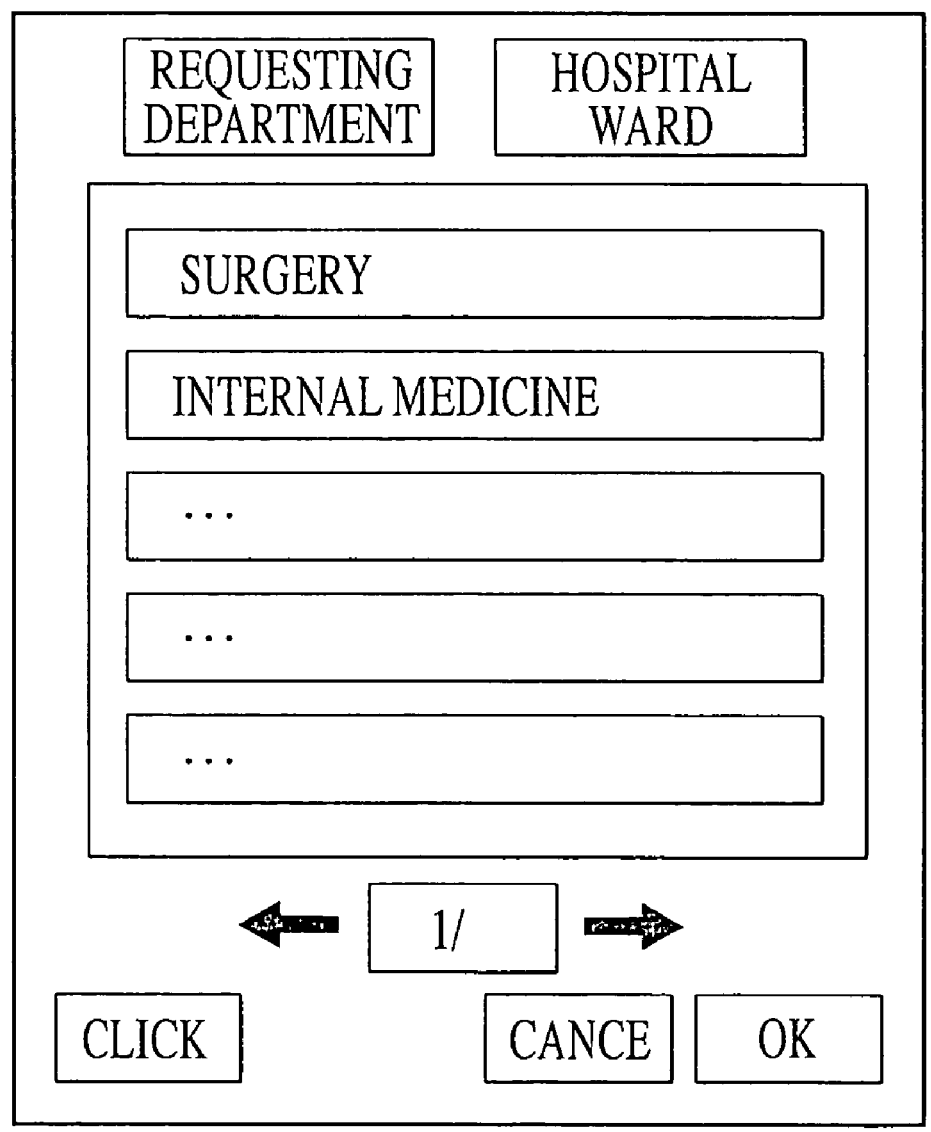
FIG. 10 is a view showing an example of the extract condition input screen to which the extract condition displayed on the display unit 13 of the portable terminal 10 is input.

Specifically, CPU 11 and RAM 15 read out from the storage apparatus 16 the radiograph pre-processing program and the radiograph start processing program, and carry out the after-mentioned radiograph pre-processing (refer to FIG. 6B) and radiograph start processing (refer to FIG. 10). Here, each processing will be described later in details.

The operating unit 12 has a cursor key, a numerical key, and various functional keys, and outputs the pushed signal corresponding to the key pushed by the photographer. Further, the operating unit 12 has a jog dial key, and outputs to CPU 11 the command signal for scrolling (moving) the information displayed on the display unit 13 in accordance with the operation of the jog dial key. Further, when the jog dial key is pushed, the pushed signal for the displayed information is output to CPU 11. Here, the operating unit 12 may have a pointing device like a touch panel and other input apparatuses in accordance with necessity. Further, a touch key instead of the jog dial key or a combination thereof may be used.

The display unit 13 has a display such as LCD (Liquid Crystal Display) and EL display (ElectroLuminescent Display), and displays each information such as the photographing order information, the obtained patient ID, the operator ID, the cassette ID, and the radiographing apparatus ID on the basis of the display command from CPU 11.

I/F 14 is an interface for connecting the portable terminal 10 and the communication terminal 10-1. When the portable terminal 10 is mounted in the communication terminal 10-1, I/F 14 outputs the detection signal to CPU 11. Further, I/F 14 mediates the data transmission between the portable terminal 10 and the control apparatus 20 through the communication terminal 10-1 by carrying out the adjustment for the transfer speed of data and the conversion of data form.

For example, I/F 14 receives the photographing order information from the control apparatus 20, and after the photography, transmits to the control apparatus 20 the operator ID, the cassette ID, and the radiographing apparatus ID corresponded to the photographing order information.

RAM 15 has a work memory area for storing the above mentioned application program, the input command, the input data, and the processing result.

The storage apparatus 16 has a storage medium (not shown) in which the program and the data are previously stored. The storage medium stores the data processed by various application programs and various processing programs corresponding to the system program and this system program. Further, the storage medium consists of a magnetic storage medium, an optical storage medium, or semiconductor memory, and can be fixedly disposed or removably mounted in the storage apparatus 16.

Further, the storage apparatus 16 stores the photographing order information file 161 for storing the photographing order information received from the control apparatus 20. The photographing order information file 161 will be described with reference to FIG. 3. FIG. 3 is a view showing an example of the data structure of the photographing order information file 161.

As shown in FIG. 3, the photographing order information file 161 has a term for storing photographing ID, patient ID, name, sex, age, hospital room, requesting department, radiographic part, photograph number, and photograph size, and a term for storing operator ID, cassette ID, and radiographing apparatus ID capable of being obtained when the photography starts. The photographing order information file 161 stores by each photographing order information the data corresponding to each item.

The item of photographing ID has the identification code (for example, 20020101001, 20020101002, 20020101003, . . . ) uniquely allotted so as to identify the photography. The item of patient ID has an identification code (for example, 10000002, 1000005, . . . ) uniquely allotted so as to identify the patient to be photographed. The item of name has the letter information showing the name of the patient to be photographed. The item of sex has the letter information showing the sex of the patient to be photographed. The item of age has as a numerical information the age of the patient to be photographed. The item of hospital room has the letter information showing the hospital room where the photography is carried out.

The item of requesting department has the letter information showing the requesting department from which the photography is requested. The item of radiographic part has the information showing the radiographic part (for example, skull A→P, skull P→A, chest P→A, . . . ). The item of photograph number has as a numerical information the number of the medical images to be photographed (for example, 3, 4, 5, . . . ). The item of photograph size has the size of the medical image to be photographed (for example, 11×14, 14×17 or the like).

The item of operator ID has the identification code (for example, a readable barcode information on the ID card held by the operator) uniquely allotted so as to identify the operator who carried out the photography. The item of cassette ID has the identification code (for example, a readable barcode information on the cassette 50) uniquely allotted so as to identify the cassette 50 by which the photography was carried out. The item of radiographing apparatus ID has the identification code (for example, a readable barcode information on the portable radiographing apparatus 40) uniquely allotted so as to identify the portable radiographing apparatus 40 by which the photography was carried out.

Further, the above mentioned datum of operator ID, cassette ID, radiographing apparatus ID are not stored in the photographing order information file 161 before the photography starts. Each data read by the barcode reader 17 is stored when the photography starts.

Further, the photographing order information may have various patient information, for example such as name of doctor in attendance, warning information for warning epidemics, presence of drug allergy, presence of pregnant, additional clinical history, necessity of special care such as invalid chair and bier, name of clinic test, secret information, other than patient ID, name, sex, and age of the patient information. Further, the photographing order information may have various photographing information, for example such as photographing method (simple photography, contrast photography or the like) and photographing date other than radiographic part, radiographing apparatus, photograph number, and photograph size of the photographing information, if anything, may be displayed by inputting barcode.

The barcode reader 17 is an example of obtaining the operator ID, the cassette ID, the photographing ID or the like, and has a scanner that is a optical reading apparatus. The barcode reader 17 reads the barcode by the scanner and obtains the information shown in the barcode by decoding it in accordance with the predetermined rule. For example, the barcode reader 17 reads the barcode on the ID card of the operator when the photography is carried out, obtains the operator ID, reads the barcode on the cassette 50 for recording the medical image, and obtains the cassette ID.

Further, the barcode reader 17 reads the barcode on a part of the bedside of patient or the body of patient, obtains the patient ID, reads the barcode on the radiographing apparatus, and obtains the radiographing apparatus ID. Further, the predetermined rule is JAN code, UPC code, CODE39, CDE93, CODE128, NW-7, INDUSTRIAL, 2of5, ITF logical code or the like.

Figure 4:
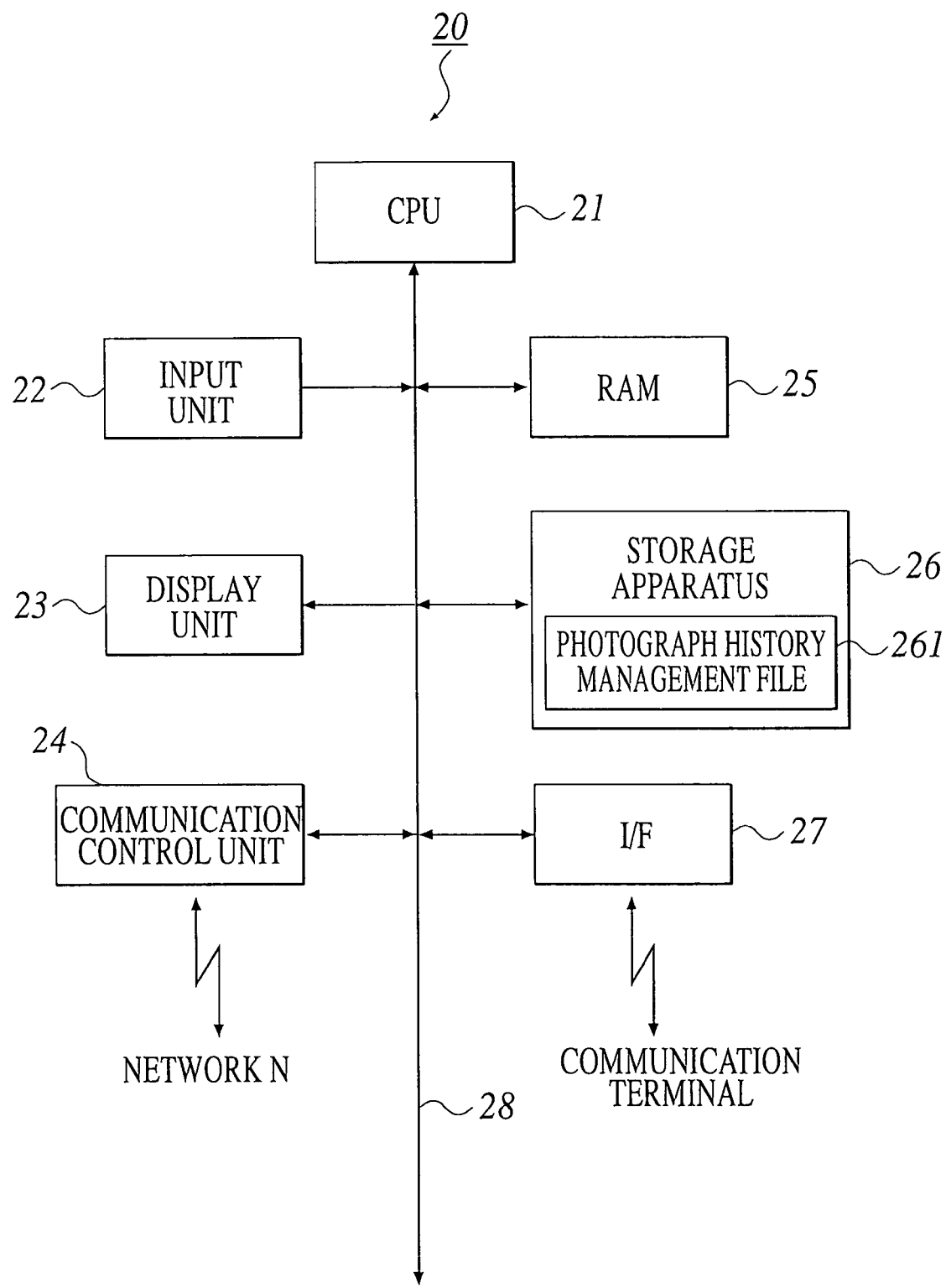
FIG. 4 is a block diagram showing a substantial structure of the control apparatus 20 shown in FIG. 1.

FIG. 4 is a block diagram showing a functional structure of the control apparatus 20. As shown in FIG. 4, the control apparatus 20 has CPU 21, an input unit 22, a display unit 23 for displaying, a communication control unit 24, RAM 25, a storage apparatus 26, I/F 27 for communicating or the like. Each unit is connected by a bus 28.

CPU 21 reads out the system program and various control program stored in the storage apparatus 26, extracts in RAM 25, and carries out as a control unit the central control for each unit by cooperating with the control program extracted in RAM 25. Further, CPU 21 carries out various processing in accordance with the program extracted in RAM 25, and displays on the display unit 23 the processing result while temporarily storing it in RAM 25.

Specifically, CPU 21 and RAM 25 read out the radiograph preparation processing program and the radiograph post-processing program from the storage apparatus 26, and carries out the after mentioned radiograph preparation processing (refer to FIG. 6A) and the radiograph post-processing (refer to FIG. 14).

The input unit 22 includes a keyboard having a cursor key, a numerical key, and various function key, and outputs to CPU 21 the pushed signal corresponding to the key pushed on the keyboard. Further, the input unit 22 may have a pointing device such as a mouse and a touch panel and other input apparatuses in accordance with necessity.

The display unit 23 has LCD, CRT (Cathode Ray Tube), and EL display, and displays the command and the data inputted from the input unit 22 in accordance with the display signal inputted from CPU 21.

The communication control unit 24 has LAN card, a router, TA (Terminal Adapter) or the like, and controls the communication between each apparatus connected by the network N through the communication line such as an exclusive line and ISDN line.

In various processing to be carried out and controlled by CPU 21, RAM 25 forms the storage area for temporarily stores the system program, the control program, the input or output data, the parameter or the like which was read from the storage apparatus 26 which can be executed in CPU 21.

The storage apparatus 26 has HDD (Hard Disc Drive), a nonvolatile semiconductor memory or the like, and stores various processing programs and the processing result corresponding to the system program practicable in CPU 21 and this system program. Further, the storage apparatus 26 has a record medium (not shown) in which the program and the data are previously stored. The record medium consists of a magnetic and optical record medium or the semiconductor memory, and is fixedly or removably mounted in the storage apparatus 26. These various programs are stored in the form of the program code readable in CPU 21.

Further, the storage apparatus 26 of the control apparatus 20 stores the photographing order information file (not shown) for storing the photographing order information received from the information management apparatus 60 and the photograph history management file 261 for managing the photograph history of the medical image. Further, because the photographing order information file is the approximately same structure as the above mentioned photographing order information file 161 (refer to FIG. 3), the illustration and the description thereof is omitted. The photograph history management file 261 will be described with reference to FIG. 5.

FIG. 5 is a view showing an example of the data structure of the photograph history management file 261. As shown in FIG. 5, photographing ID, photographing date, operator ID, cassette ID, radiographing apparatus ID, reading apparatus ID, and error flag is housed in the item of the photograph history management file 261.

The item of photographing ID has the identification code (for example, 20020101001, . . . ) for uniquely identifying the photographing order information stored in the above mentioned photographing order information file 161, and the above mentioned photographing order information is corresponded therewith by the photographing ID. The item of photographing date has the information (for example, 2003/3/3, . . . ) showing the date that the medical image was photographed.

The item of operator ID has the identification information (for example, sato1234, . . . ) for uniquely identifying the operator who photographed the medical image. The item of cassette ID has the identification information (for example, 04000108022016, . . . ) for uniquely identifying the cassette 50 in which the medical image was stored. The item of radiographing apparatus ID has the identification information (for example, A101010, . . . ) for uniquely identifying the radiographing apparatus by which the medical image was photographed or the portable radiographing apparatus 40.

The item of reading apparatus ID has the identification information (for example, E1100101, . . . ) for uniquely identifying the medical image reading apparatus 30 by which the medical image was read from the cassette 50. The item of error flag is input the check flag showing the presence of error in the medical image.

Further, the above mentioned photographing ID, photographing date, operator ID, cassette ID, and radiographing apparatus ID are the information to be transmitted from the portable terminal 10 in the after mentioned radiograph post-processing. The reading apparatus ID is the information to be transmitted from the medical image reading apparatus 30. Further, the presence of check for the error flag is the information to be input by the operator or if anything, a radiograph operator. Further, the information stored in the photograph history management file 261 is not limited to the above example, and otherwise can store various information in accordance with necessity.

I/F 27 is an interface for connecting the control apparatus 20 and the communication terminal 10-1. When the portable terminal 10 is mounted in the communication terminal 10-1, I/F 27 outputs the detection signal to CPU 21. Further, I/F 27 mediates the data transmission between the portable terminal 10 and the control apparatus 20 through the communication terminal 10-1 by carrying out the adjustment for the transfer speed of data and the conversion of data form. For example, I/F 27 transmits the photographing order information to the portable terminal 10 before the photography, and after the photography, receives from the portable terminal 10 the operator ID, the cassette ID, and the radiographing apparatus ID corresponded to the photographing order information Subsequently, the medical image reading apparatus 30 will be described. Further, because the functional structure of the medical image reading apparatus 30 is approximately the same structure as the above mentioned control apparatus 20, the same part is indicated the corresponding name and the illustration and description thereof are omitted. That is, the medical image reading apparatus 30 has CPU 31, an input unit 32, a display unit 33, a communication control unit 34, RAM 35, a storage apparatus 36, an image reading unit 37, and a barcode reader 38, and each unit is connected by the bus 39.

The image reading unit 37 irradiated the excitation light to the photostimulable phosphor layer of the cassette 50, makes the fluorescence equal to the accumulated radiation energy emit, photoelectrically converts the emitted fluorescence, and obtains the radiation image data.

The barcode reader 38 is an example of obtaining the cassette ID, and has a scanner which is a optical reading apparatus. The barcode reader 38 reads the barcode on the surface of the cassette 50 attached to the image reading unit 37.

CPU 31 obtains the medical image read by the image reading unit 37, the cassette ID read by the barcode reader 38, and the reading apparatus ID for uniquely identifying the medical image reading apparatus by which the medical image was read, controls the communication control unit 34, corresponds the cassette ID and the reading apparatus ID to the medical image, and transmits it to the control apparatus 20. Here, it is preferable that the cassette ID and the reading apparatus ID to be corresponded to the medical image are transmitted, for example, on the basis of DICOM (Digital Imaging and Communications Medicine) rule.

Next, the operation of the embodiment will be described.

Further, the program for realizing each function described in the after mentioned flowcharts is stored the storage apparatus 16 of the portable terminal 10, the storage apparatus 26 of the control apparatus 20, or the storage apparatus 36 of the medical image reading apparatus 30 in the form of the program code readable by the computer. CPU 11 of the portable terminal 10, CPU 21 of the control apparatus 20, or CPU 31 of the medical image reading apparatus 30 subsequently execute the operation of the program code by cooperating with each program extracted by RAM 15, RAM 25, or RAM 35.

First, as a preparation processing for the photography, a first radiograph preparation processing in which the photographing order information is obtained from the control apparatus 20 to the portable terminal 10. The first radiograph preparation processing is executed by extracting to RAM 25 the first radiograph preparation processing program read from the storage apparatus 26 by CPU 21, because the input or the like from the operator for the input unit 22 of the control apparatus 20 and for commanding the execution of the first preparation processing is a trigger.

Further, the photographing order information is previously transmitted from the information control apparatus 60 through the network N to the control apparatus 20, and stored in the storage apparatus 26. Otherwise, the photographing order information is input for setting and stored in the storage apparatus 26. Further, the photographing order information may be displayed on the display unit 23.

Figure 6A:
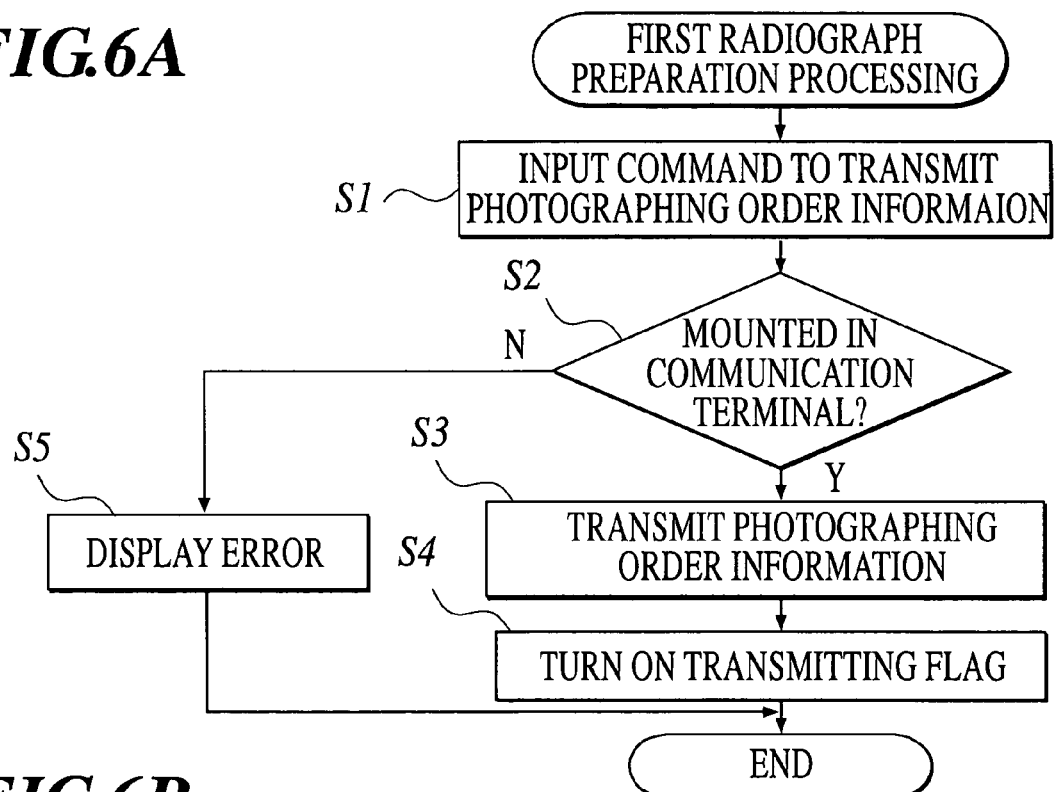
FIG. 6A is a flow chart showing a first radiograph preparation processing executed by the control apparatus 20 and FIG. 6B is a flow chart showing a first radiograph pre-processing executed by the portable terminal 10.

FIG. 6A is a flowchart showing the first radiograph preparation processing executed by CPU 21 of the control apparatus 20. As shown in FIG. 6A, when the transmitting command of the photographing order information is input through the input unit 22 by the operator (step S1), the control of I/F 27 determines whether the portable terminal 10 is mounted in the communication terminal 10-1 or not (step S2). Here, when the portable terminal 10 is not mounted in the communication terminal 10-1 (step S2; NO), the error is displayed on the display unit 23 (step S5), and the photographing preparation processing is finished.

Meanwhile, when the portable terminal 10 is mounted in the communication terminal 10-1 (step S2; YES), the photographing order information is obtained from the storage apparatus 26, the photographing order information is transmitted through the communication terminal 10-1 to the portable terminal 10 (step S3), the transmitting flag of the transmitted photographing order information is turned on (step S4), and the first radiograph preparation processing is finished. In step S3, the control apparatus 20 extracts the photographing order information for each portable terminal 10 from all photographing order information, and sends it to not less than one portable terminal 10 connected therewith.

Figure 6B:
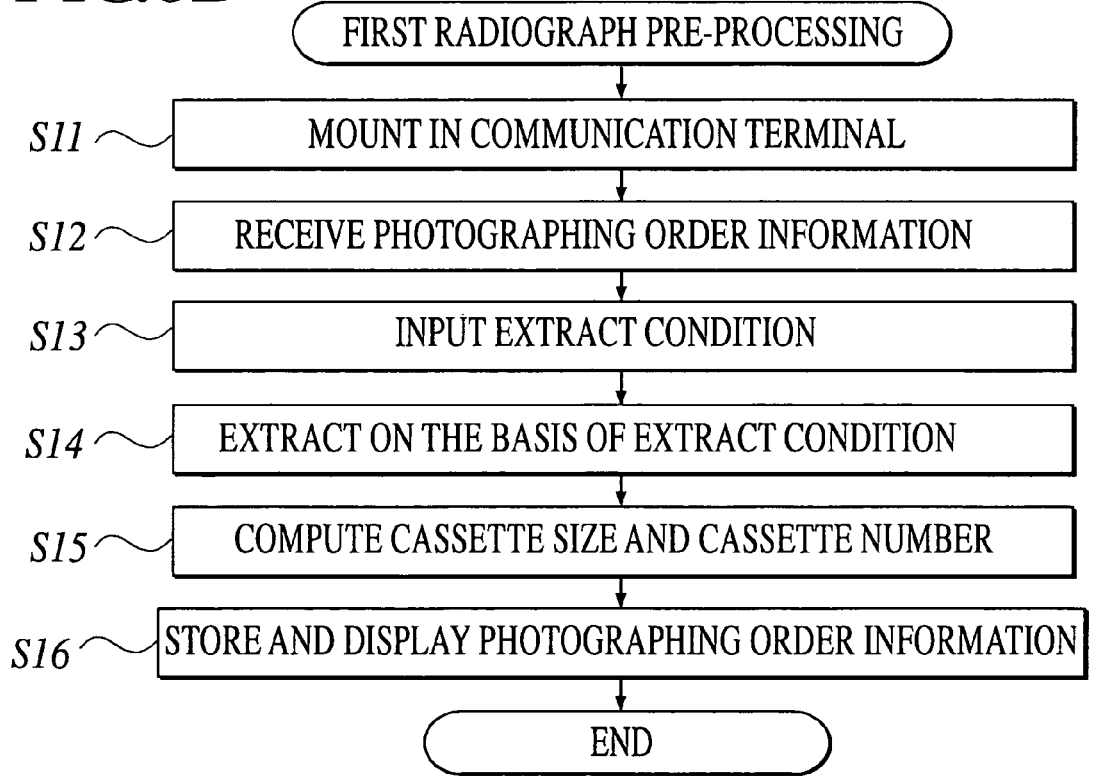

FIG. 6B is a flowchart showing the first radiograph pre-processing executed by the portable terminal 10. The first radiograph pre-processing is executed by extracting to RAM 15 the first radiograph pre-processing program read from the storage apparatus 16 by CPU 11, because the mounting of the portable terminal 10 in the communication terminal 10-1 by the operator is a trigger. As shown in FIGS. 6A and 6B, the portable terminal 10 is finished being mounted in the communication terminal 10-1 to obtain the photographing order information (step S11).

Next, the photographing order information to be transmitted from the control apparatus 20 is received by the control of I/F 14 (step S12). Further, the extract condition input screen is displayed on the display unit 13, and the operator who is a user of the portable terminal 10 inputs the extract condition from the operating unit 12 (step S13). The extract condition is, for example, each patient ID, each operator ID, order of photographing patient, each area (hospital ward, floor, or the like), or the photography finished or unfinished. Further, the extract condition may be a combination thereof.

Further, the photographing order information is extracted on the basis of the extract condition input in step S13 (step S14). Further, the size and the number of cassette necessary for the photography are computed from the photographing order information (specifically, the size and the number of photograph) extracted in step S14 (step S15). Further, the photographing order information including as an additional information the computed size and the number of cassette is stored in the photographing order information file of the storage apparatus 16, the photographing order information is displayed on the display unit 13 (step S16), and the first radiograph pre-processing is finished.

The operator for photographing the patient can easily and reliably prepare the cassette 50 necessary for the photography without any other works, by referring to the photographing order information, the size and the number of cassette displayed on the portable terminal 10.

In the above described radiograph preparation processing, the screen displayed on the display unit 23 of the control apparatus 20 will be described with reference to FIGS. 7 to 9.

Figure 7:
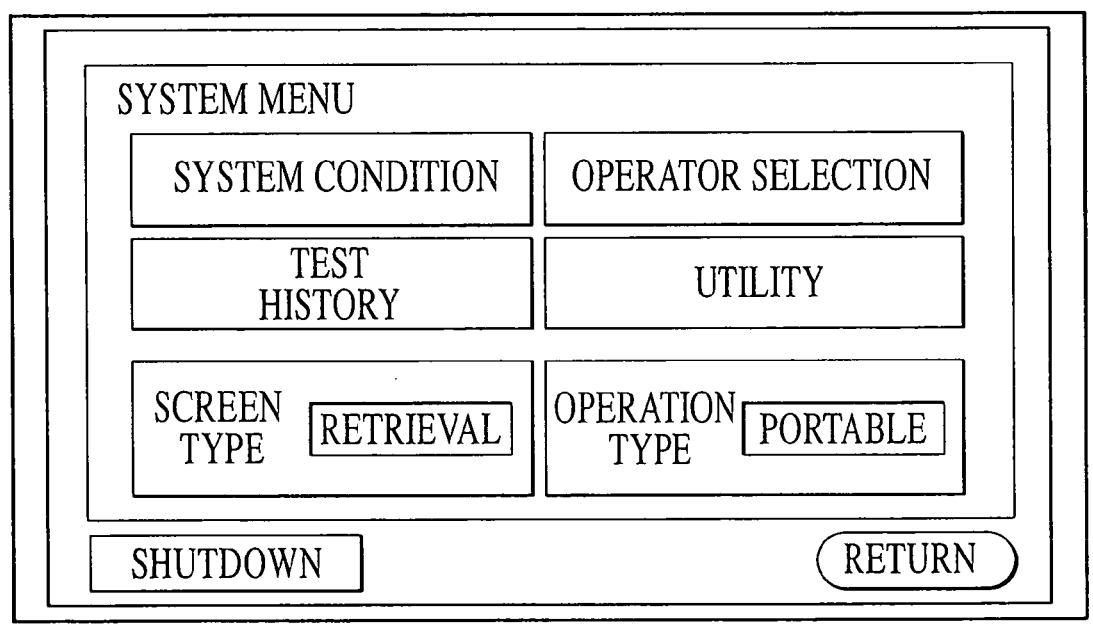
FIG. 7 is a view showing an example of the menu screen displayed on the display unit 23 of the control apparatus 20.

FIG. 7 is a view showing the menu screen 231 for selecting the desired processing. As shown in FIG. 7, the menu screen 231 has a command button for commanding each menu of "SYSTEM CONDITION", "OPERATOR SELECTION", "TEST HISTORY", "UTILITY", "SCREEN TYPE", and "OPERATION TYPE." Further, the command buttons of "SCREEN TYPE" and "OPERATION TYPE" have an input item. For example, when "PORTABLE" is input on the input item of the "OPERATION TYPE" and the button is commanded, a portable mode screen of the case that the photography is carried out by the portable radiographing apparatus 40 is displayed. Further, "NORMAL" is input to the input item of "OPERATION TYPE," the normal mode screen of the case that the photography is carried out in the normal radiographing room.

FIG. 8 is a view showing the portable list screen 232 on which the photographing order information is displayed at sight in the portable mode. As shown in FIG. 8, the portable list screen 232 has the area for displaying the photographing order information and the area for displaying the command button for commanding various commands. The area for displaying the photographing order information has each item for displaying patient ID, tub type, name, sex, birth date, radiographic part, photograph number (the number of photograph), and suspend. Each item displays the data respectively corresponding thereto. The drawing of the photograph size is omitted.

Further, in the right edge and the bottom of the portable list screen 232, the area for displaying the command button for inputting various commands has a command button on which each text data of "TRANSMIT", "RECEIVE", "NEW/RETRIEVAL", "MODIFY", "DELETE", . . . , and "CONFIRMATION SCREEN" other than selection keys is displayed. The corresponding command is input by operating each command button through the input unit 22. For example, the photographing order information displayed on the portable list screen 232 is selected by selection keys. When the command button of "TRANSMIT" is operated, the selected photographing order information is transmitted to the portable terminal 10. Here, when the photographing order information is transmitted to the portable terminal 10, the transmitting finish flag of the photographing order information is turned on, and the term of "TAB TYPE" displays the check flag "→" indicating the photographing order information is finished being transmitted. Further, when "NEW/RETRIEVAL" command button is operated, input screens 233 and 234 for newly registering the photographing order information are displayed.

Figure 9B:
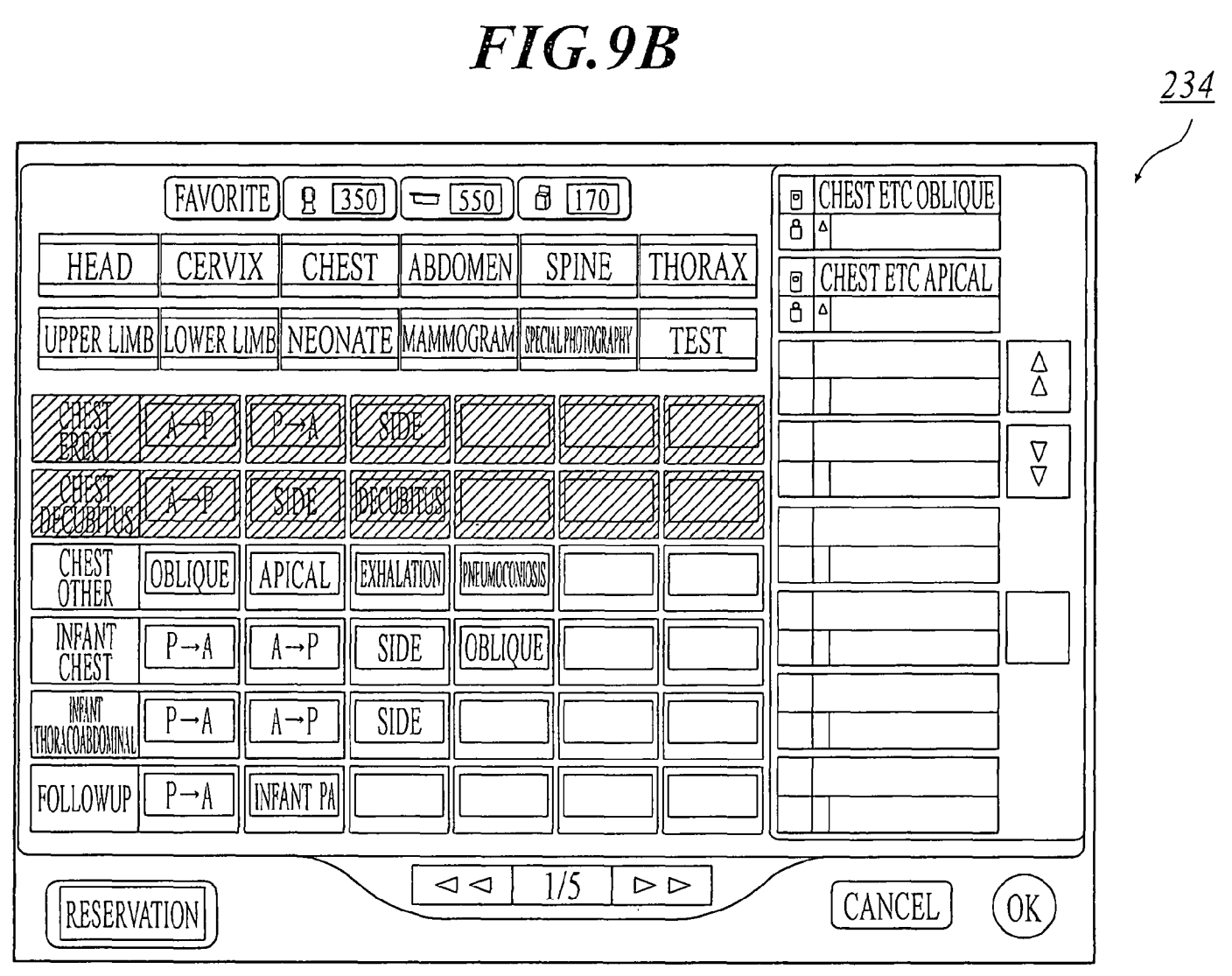

FIGS. 9A and 9B are views showing the input screens 233 and 234 to be displayed when "NEW/RETRIEVAL" command button is operated in the above described portable list screen 232. FIG. 9A is a view showing the input screen 233 for newly inputting the patient information out of the photographing order information. As shown in FIG. 9A, the input screen 232 has the area on which the patient information is input and the area on which the letter key for inputting letters is displayed.

The area on which the patient information displayed on the upper step of the input screen 233 is input has each item for inputting patient ID, patient name (roman letter, kana, kanji), sex, birth date, and comment. The input data is displayed on the corresponding item in accordance with the operation of the input unit 22. Further, in the area on which the letter key displayed on the lower step of the input screen 233 is displayed, the key-in corresponding to the letter key displayed is carried out by a mouse or a touch panel included in the input unit 22. Further, the key-in may be carried out by a keyboard included in the input unit 22.

FIG. 9B is a view showing the input screen 234 for newly inputting the photographing information out of the photographing order information. As shown in FIG. 9B, the photographing information input screen 234 has the area on which the command button for commanding as the radiographing condition the radiographic part is displayed, the area of the command button for commanding the radiographing direction in the radiographic part, and the area on which the input radiographic part and radiographing direction are displayed are displayed.

The area on which the command button of the radiographic part to be displayed on the left upper step of the input screen 234 has a command button on which each text data of, for example, "HEAD", "CERVIX", . . . , "TEST" is displayed. The corresponding radiographic part is selected because each command button is commanded through the input unit 22. Further, in the area on which the command button of the radiographing direction displayed on the left middle step of the input screen 234 is displayed, a screening display is executed. The meshed part cannot be selected in the portable mode. Specifically, the radiographing part displayed on the area shows a radiographing part incapable of being photographed by the portable radiographing apparatus 40. Further, as a displaying method incapable of being selected, other than the screening display, a non-display or inactive display is applicable. Further, when the command button incapable of being selected is commanded, an audio or image warning may be output.

Further, the area on which the command button of the radiographing direction displayed on the left bottom step of the input screen 234 has, as a radiographing direction of the radiographic part of "CHEST OTHER" for example, the command button on which each text data of "OBLIQUE", . . . , "PNEUMOCONIOSIS" is displayed. The corresponding radiographing direction is selected by commanding each command button through the input unit 22. Further, in the area on which the radiographic part and the radiographing direction displayed on the right of the input screen 233, the radiographic part and the radiographing direction selected by commanding the above described command button is displayed for example as "CHEST ETC OBLIQUE."

Further, the above described radiograph pre-processing screen will be described with reference to FIGS. 10 and 11. FIG. 10 is a view showing the extract condition input screen 13A to which the extract condition is input. As shown in FIG. 10, the extract condition input screen 13A is a screen for selecting as an example of the extract condition the condition of the requesting department (internal medicile, suegery or the like). The extract condition input screen 13A has the item of extract condition, the detailed item of each item, and the command button for inputting "CLICK (SELECT)", "CANCEL", and "OK." The extract condition can select an unshown item other than the shown requesting department, hospital ward, or the like. On the extract condition input screen 13A, when the extract condition is selected and then the OK button is selected, the extract condition is input.

FIG. 11 is a view showing the extract result screen 13B of the extracted photographing order information. The extract result screen 13B has the extract condition, the case number in which the cassette 50 is registered with respect to the photograph corresponding to the extract condition, the unregistered case number, the total case number, and the command button for inputting "CANCEL" and "OK." Here, the display of the photographing order information of the case that "CHEST-CHEST DECUBITUS" of the radiographic part is input as the extract condition is shown. In the after described radiograph start processing, the extract result screen 13B is an example of displaying as the case number (for example, the number of patients to be photographed) whether the extracted photographing order information is corresponded to the cassette 50 and registered or not. When only radiograph pre-processing is executed, an unregistered case is displayed. For example, when the unregistered "10 cases" (not shown) are selected, the photograph size, the photograph number, and the photographing order information corresponding to the case (photography) are displayed. The operator can easily and reliably prepare the cassette 50 in accordance with the unregistered photographing order information.

Next, the radiograph start processing will be described. The radiograph start processing corresponds the patient ID and the photographing order information by the portable terminal 10, corresponds the photographing order information, the operator ID, the cassette ID, and the radiographing apparatus ID, and records them in the hospital room where the photography is carried out before the photography.

Figure 12:
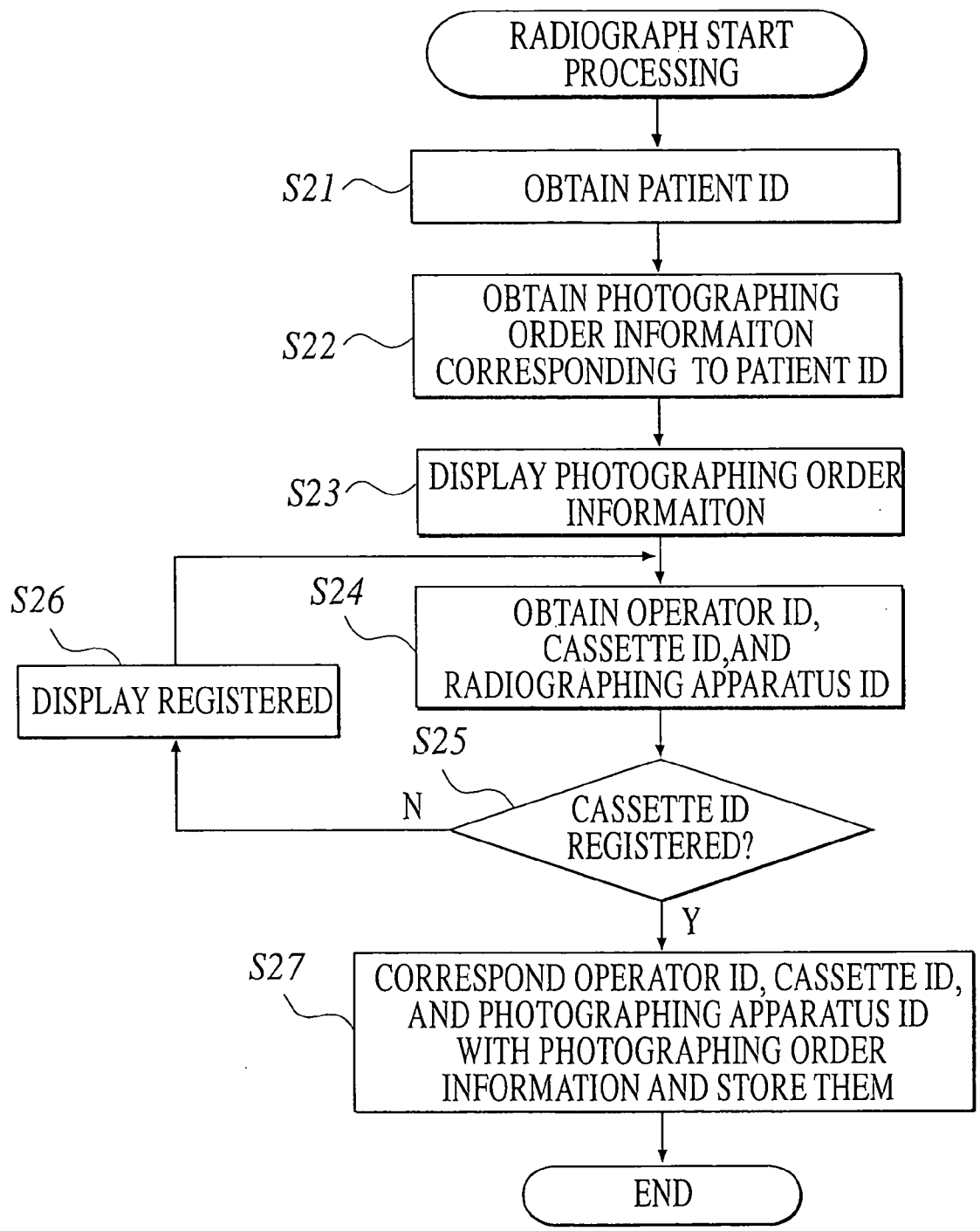
FIG. 12 is a flow chart showing the radiograph start processing executed by the portable terminal 10.

FIG. 12 is a flowchart showing the radiograph start processing executed by the portable terminal 10. The radiograph start processing is executed by extracting to RAM 15 the radiograph start processing read out from the storage apparatus 16 by CPU 11, because the input or the like from the operator for the operating unit 12 of the portable terminal 10 and for commanding the execution of the radiograph start processing is a trigger. The barcode on a part of the bedside of patient or the body of patient is read by the control of the barcode reader 17, and the patient ID is obtained (step S21). Next, the photographing order information corresponding to the read patient ID is obtained from the storage apparatus 16 (step S22).

Subsequently, while the obtained photographing order information is displayed on the display unit 13 (step S23), each barcode on the operator for the photography, the cassette 50, and the portable radiographing apparatus 40 is read by the control of the barcode reader 17, and the operator ID the cassette ID, and the photographing order information ID are obtained (step S24). Further, whether the cassette ID obtained in step S24 is registered or not is identified (step S25). If there is a plurality of cassettes to be prepared by the operator, it is convenient to detect the cassette which was registered only once or more. Specifically, whether the obtained cassette ID is already recorded (registered) or not in the storage apparatus 16 is identified.

If the obtained cassette ID is already registered (step S25; YES), the fact that the cassette ID is registered is notified to the display unit 13 (step S25) and the obtained cassette ID is back to step S24. If the obtained cassette ID is not yet registered (step S25; NO), the obtained operator ID, cassette ID, and photographing ID are corresponded to the photographing order information and stored in the storage apparatus 16 (step S27) because the obtained cassette ID is not yet registered, and the radiograph start processing is finished.

In the above described radiograph start processing, the screen displayed on the display unit 13 of the portable terminal 10 will be described with reference to FIGS. 13A and 13B. FIG. 13A is a view showing the patient list screen 131 on which the patient registered in the portable terminal 10 is displayed at sight. As shown in FIG. 13A, the patient list screen 131 has the area showing the patient information. The area has each item displaying patient ID, patient name, and hospital ward. Specifically, the number data "1001" is displayed in the patient ID. The text data of "ICHIRO YAMADA" is displayed in the item of name.

FIG. 13B is a view showing the screen 132 on which the photographing order information of the corresponding patient is displayed if the patient ID is obtained from the barcode reader 17 of the portable terminal 10. As shown in FIG. 13B, the screen 132 has the area for displaying the patient information and the area for displaying the photographing information. The area for displaying the patient information has each item for displaying patient name, patient ID, sex, hospital ward, and hospital room. Each item displays the corresponding item.

Further, the area for displaying the photographing information has each item for displaying radiographic part, cassette ID, operator ID, radiographing apparatus ID, the photograph number, and photograph size. Each item of cassette ID, operator ID, and radiographing apparatus ID displays the data obtained from the barcode reader 17 of the portable terminal 10 at the same time as the data is read. Specifically, each item of radiographic part and photograph size displays the text data of "CHEST ETC OBLIQUE 11×14." The item of cassette ID displays the numerical data of "04000108022016." Further, the item of operator ID displays the text data and the numerical data of "suzuki 777." The item of radiographing apparatus ID displays the text data and the numerical data of "A101010."

Further, the operator photographs the patient corresponding to the photographing order information by using the portable radiographing apparatus 40 and the cassette 50 registered in the radiograph start processing with reference to the photographing order information displayed in the portable terminal 10. The photographing order information photographed through the input unit 22 by the operator is input to the portable terminal 10. The portable terminal 10 transmits to the control apparatus 20 the operator ID, the cassette ID, and the radiographing apparatus ID corresponded to the photographing order information with its photography finished. The medical image reading apparatus 30 reads the medical image, the cassette ID, and the reading apparatus ID from the photographed cassette 50 and transmits them to the control apparatus 20.

Subsequently, after the photography, the control apparatus 20 obtains the operator ID, the cassette ID, and the radiographing apparatus ID corresponded to the photographing order information with its photography finished from the portable terminal 10, while obtains the medical image, the cassette ID, and the reading apparatus ID read from the medical image reading apparatus 30.

FIG. 14 is a flowchart showing the radiograph post-processing executed by the control apparatus 20. As shown in FIG. 14, the radiograph post-processing is executed by extracting to RAM 25 the radiograph post-processing program read from the storage apparatus 26 by CPU 21, because the input or the like from the operator for the input unit 22 of the control apparatus 20 and for commanding the execution of the radiograph post-processing is a trigger. When the operator ID, the cassette ID, and the radiographing apparatus ID corresponded to the photographing order information with its photography finished are received from the portable terminal 10 through the communication terminal 10-1 (step S31; YES), the operator ID, the cassette ID, and the radiographing apparatus ID are corresponded to the photographing order information and stored in the photograph history management file 261 (step S32). Further, the receiving finish flag is turned on with respect to the photographing order information in which the operator ID, the cassette ID, and the radiographing apparatus ID are received (step S33).

Next, when the medical image, the cassette ID, and the reading apparatus ID are received from the medical image reading apparatus 30 (step S32), the received reading apparatus ID is corresponded to the photographing order information and stored in the photograph history management file 261 on the basis of the cassette ID (step S35). Further, the medical image and the photographing order information are corresponded and stored in the storage apparatus 26 on the basis of the cassette ID corresponded to the medical image and the cassette ID corresponded to the photographing order information (step S36).

Further, the operator ID, the cassette ID, the radiographing apparatus ID, and the reading apparatus ID corresponding to the medical image are added as an additional information to the medical image (step S37). Here, the additional information added to the medical image is preferably added thereto on the basis of DICOM. Further, the received medical image is displayed on the display unit 23 (step S38), and the radiograph post-processing is finished.

Figure 15:
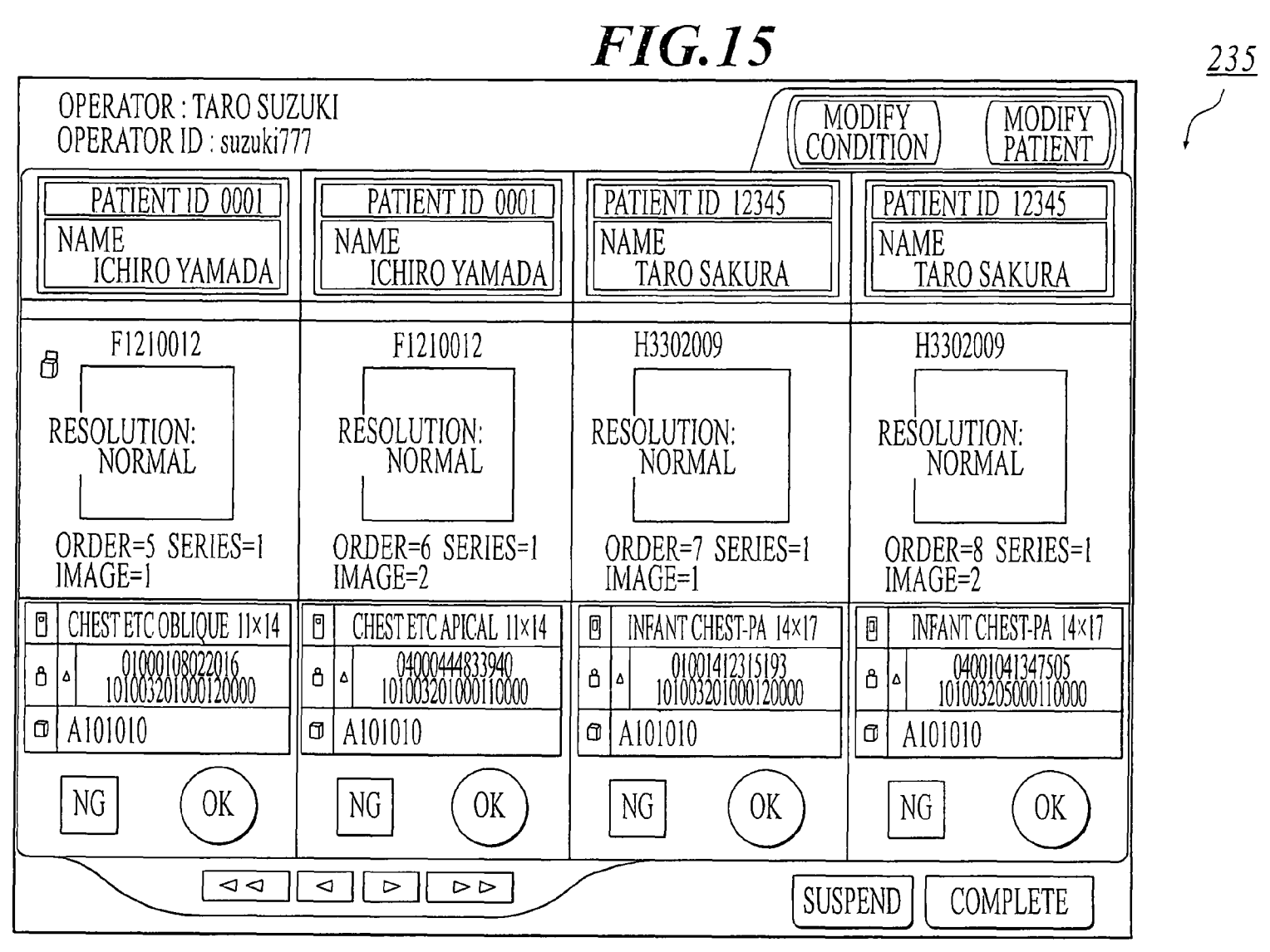

The medical image displayed on the display unit 23 of the control apparatus 20 will be described with reference to FIG. 15. FIG. 15 is a view showing the portable processing screen 235 to be displayed on the display unit 23 when the photography is carried out by using the portable terminal 10. As shown in FIG. 15, the portable processing screen 235 displays on the same screen thereof the medical image of a plurality of patients registered in one portable terminal 10.

Specifically, the portable processing screen 235 has the area for displaying the operator information and the area for displaying by each patient the patient information, the medical image, and the photographing information. 4 kinds of medical image can be displayed on screen simultaneously. Specifically, the area on which the operator information on the left upper edge of the portable processing screen 235 is displayed has the item for displaying as the operator name the text data of "TARO SUZUKI" and the item for displaying as the operator ID the text data and the numerical data of "suzuki777." Further, describing the medical image displayed on the left edge as the medical image displayed by each patient, the area for displaying the patient information has the item for displaying as the patient ID the numerical data of "0001" and the item for displaying as the name the text data of "ICHIRO YAMADA."

In the bottom thereof, the area for displaying the medical image is displayed. The medical image, the item for displaying as the reading apparatus ID the numerical data of "F1210012", and the item for displaying as the resolution the "NORMAL" text data are displayed. Further, in the bottom thereof, the area for displaying the photographing information is disposed. The item for displaying as the radiographic part and the photograph size the text data of "CHEST ETC OBLIQUE 14×11" and the item for displaying as the radiographing apparatus ID the text data of "A101010" and the numerical data are disposed.

Further, in the bottom of the area for displaying the photographing information, the command button for inputting "NG" or "OK" is disposed, and the presence of abnormality of the displayed medical image is input. Specifically, if the medical image is abnormal, the error flag of the photograph history management file 261 of the corresponding medical image is turned on after the "NG" command button is commanded through the input unit 22.

Further, the control apparatus 20 can display at sight the identification information such as the operator ID, the cassette ID, the photographing ID, and the reading apparatus ID with respect to the medical image with its error flag turned on on the basis of the photograph history management file 261 in which the presence of abnormality is stored. In the case, for example, the medical image abnormal by each identification information can be displayed by sorting it. Therefore, the operator, the cassette, the radiographing apparatus, and the reading apparatus that are often abnormal are statistically extracted, the cause of abnormality is reliably identified, and the cause can be solved at once.

As described above, according to the medical image photographing system 100 of the present invention, the photographing order information is transmitted from the control apparatus 20 to the portable terminal 10 in the radiograph preparation. In the portable terminal 10, the photographing order information is received, the photographing order information is extracted on the basis of the extract condition to be input, its size and number of cassette are computed, the size and the number of cassette, and the photographing order information are displayed.

Further, the patient ID of the patient to be photographed, the operator ID for the photography, and the cassette ID for recording the medical image, and the radiographing apparatus ID for recording the medical image are read when the photography starts, and corresponded to the photographing order information. Further, after the photography, the operator ID, the cassette ID, and the radiographing apparatus ID are corresponded to the photographing order information and transmitted from the portable terminal 10 to the control apparatus 20.

Meanwhile, in the medical image reading apparatus, the medical image and the cassette ID are read from the cassette 50 in which the medical image is recorded, and the cassette ID and the reading apparatus ID are corresponded to the medical image and transmitted to the control apparatus 20. Further, in the control apparatus 20, the operator ID, the cassette ID, the radiographing apparatus ID, and the reading apparatus ID are corresponded to the photographing order information and stored in the photograph history management file 261 and at the same time the photographing order information and medical image are corresponded and managed on the basis of the cassette ID.

Therefore, in the portable terminal 10, because the photographing order information extracted on the basis of the predetermined extract condition required by the operator and the size and the number of cassette necessary for the photography thereof are computed and displayed, the operator can easily and reliably prepare the cassette without any other works by referring to the size and the number of cassette corresponding to the extract condition and easily and reliably carry out the photography by referring to the photographing order information corresponding to the extract condition, which makes more effective the photography.

Second Embodiment

Figure 16:
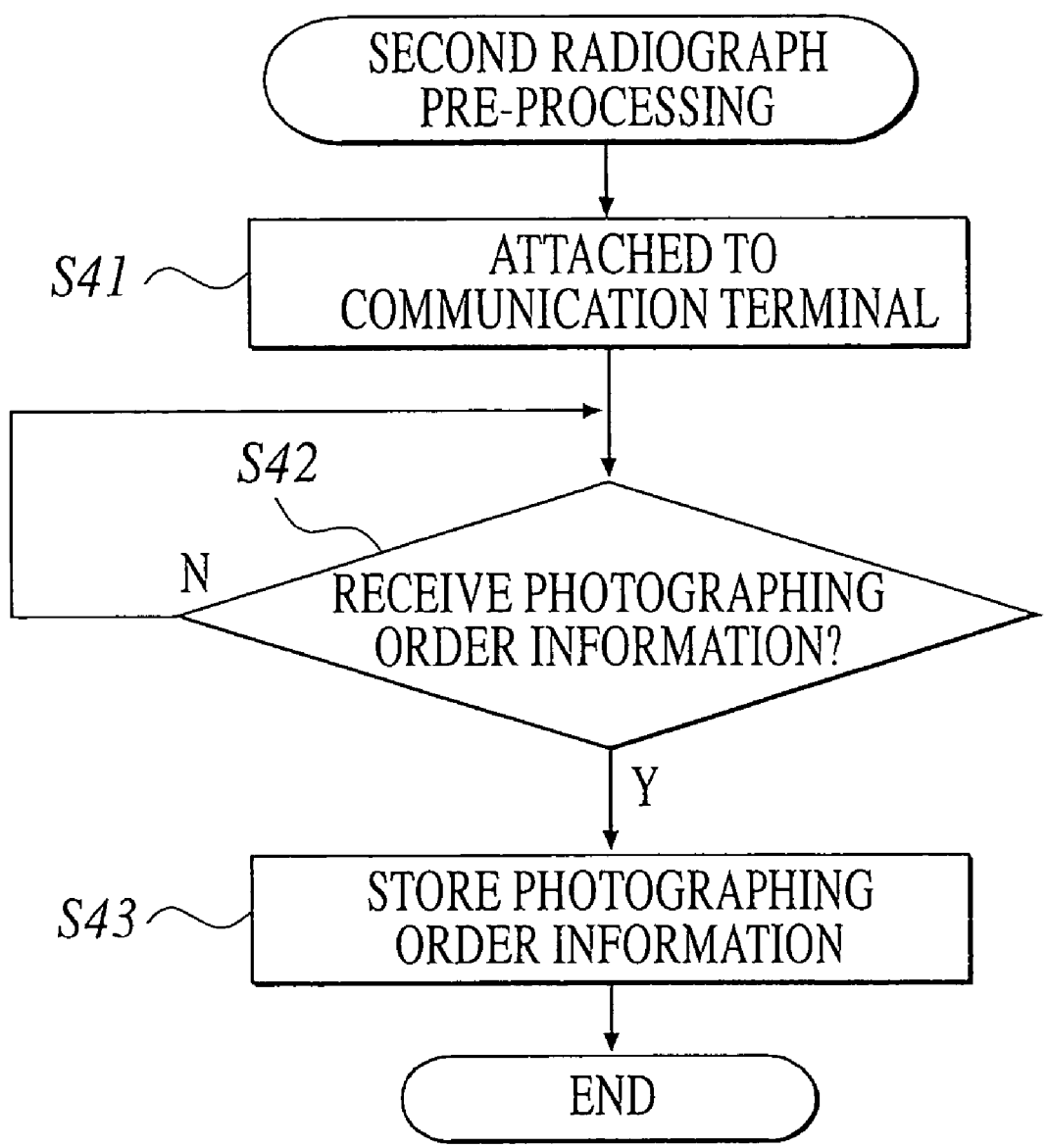
FIG. 16 is a flow chart showing a second radiograph pre-processing executed by the portable terminal 10.
Figure 17:
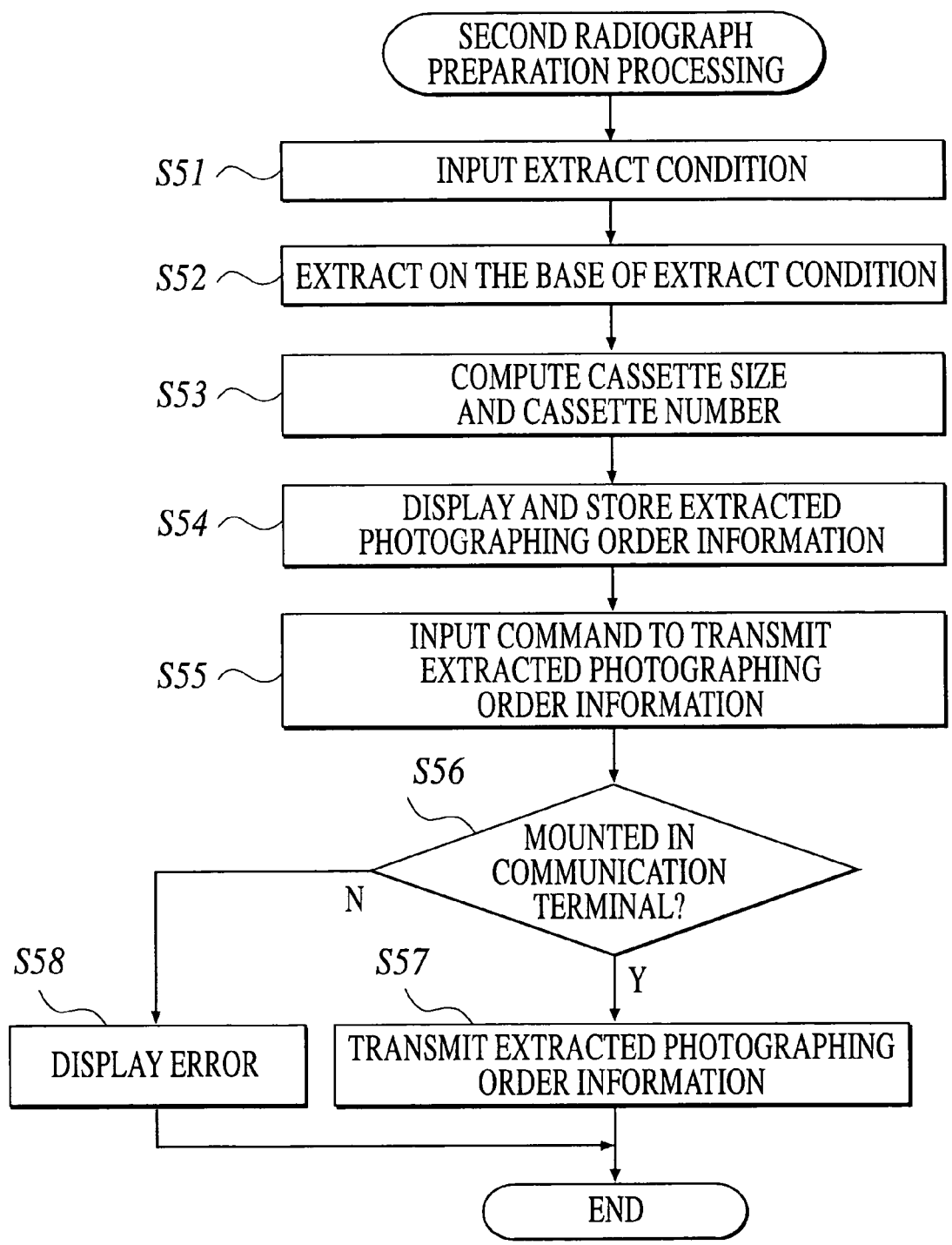
FIG. 17 is a flow chart showing a second radiograph preparation processing executed by the control apparatus 20.

The structure of the second embodiment will be described with reference to FIGS. 16 and 17. FIG. 16 is a flowchart showing a second radiograph pre-processing executed in the portable terminal 10. FIG. 17 is a flowchart showing a second radiograph preparation processing executed in the control apparatus 20.

The embodiment of the present invention is the same as the medical image photographing system 100 of the first embodiment with respect to the structure thereof. Further, for the operation of the medical image photographing apparatus 100, the first radiograph preparation processing, the second radiograph pre-processing, and the second radiograph preparation processing shown in FIG. 6A are executed. Therefore, the part mainly different from the first embodiment will be described.

In the control apparatus 20 of the embodiment, the photographing order information of the portable terminal 10 to be transmitted is extracted, displayed, and transmitted to the portable terminal 10. In the portable terminal 10, the photographing order information is received and displayed. In the embodiment, for example, a plurality of portable terminals 10 is controlled with respect to one control apparatus 20. These portable terminals 10 are exclusive use for each radiologist (operator).

The operation of the embodiment of the medical image photographing system 100 will be described. In the control apparatus 20, the first radiograph pre-processing of FIG. 6A of the first embodiment is previously executed. The photographing order information for each portable terminal 10 is transmitted to each portable terminal 10.

Here, the second radiograph pre-processing executed in the portable terminal 10 will be described with reference to FIG. 16. The second radiograph pre-processing is executed by extracting to RAM 15 the second radiograph pre-processing program read out from the storage apparatus 16 by CPU 11, because mounting by the operator the communication terminal 10-1 to the portable terminal 10 is a trigger.

First, the portable terminal 10 is finished being mounted in the communication terminal 10-1 by the operator to obtain the photographing order information (step S41). The portable terminal 10 mounted in the communication terminal 10-1 receives the photographing order information from the control apparatus 20 through the communication terminal 10-1 if the photographing order information thereof from the control apparatus 20 is transmitted. Further, whether the photographing order information is received from the control apparatus 20 or not is determined (step S42). If the photographing order information is not received from the control apparatus 20 (step S42; NO), the photographing order information is back to step S42.

If the photographing order information is received from the control apparatus 20 (step S42; YES), the photographing order information received from the control apparatus 20 is stored in the photographing order information file 161 of the storage apparatus 16 (step S43), and the second radiograph pre-processing is finished. In step S53, the received photographing order information may be displayed in the display unit 13.

Next, the second radiograph preparation processing for transmitting to the portable terminal 10 to which the photographing order information is extracted, displayed, and transmitted from the control apparatus will be described. The second radiograph preparation processing is executed by extracting to RAM 25 the second radiograph preparation processing program read out from the storage apparatus 26 by CPU 21, because the input or the like from the operator for the input unit 22 of the control apparatus 20 and for commanding the execution of the second preparation processing is a trigger.

First, by the execution of the first radiograph preparation processing shown in FIG. 6A, the photographing order information transmitted to the portable terminal 10 is stored in the storage apparatus 26. Further, as shown in FIGS. 6A and 6B, the extract condition input screen is displayed on the display unit 23, and the extract condition is input from the input unit 22 by the operator who is a user of the portable terminal 10 (step S51). Although the extract condition is the same as the extract condition in step S13 of the first radiograph pre-processing of FIG. 6B, for example, the extract condition also has the information for identifying the portable terminal 10 (the portable terminal 10 for which the photographing order information is extracted) to be used by the operator. Relating to this, the extract condition may have the portable terminal ID for example. Further, if each operator and each portable terminal 10 are corresponded, the extract condition may include the operator ID.

Further, the photographing order information of the portable terminal 10 to be extracted is extracted on the basis of the extract condition input in step S51 (step S52). Further, the size and the number of cassette necessary for the photography are computed by the photographing order information (specifically, the size and the number of photograph) extracted in step S42 (step S53). Further, the photographing order information (or the extracted photographing order information) extracted in step S52 and including as the additional information the size and the number of cassette computed in step S53 is stored in the photographing order information file 161 of the storage apparatus 26. The extracted photographing order information is displayed on the display unit 23 (step S54). Further, the command for transmitting the extracted photographing order information is input through the input unit 22 by the operator (step S55). Further, by the control of I/F 27, whether the portable terminal 10 (hereinafter referred to as the portable terminal 10 to be transmitted) corresponding to the extracted photographing order information is mounted in the communication terminal 10-1 is identified (step S56).

Here, if the portable terminal 10 to be transmitted is not mounted in the communication terminal 10-1 (step S56; NO), error is displayed on the display unit 23 (step S58) and the second radiograph preparation processing is finished. Meanwhile, if the portable terminal 10 to be transmitted is mounted in the communication terminal 10-1 (step S56; YES), the extracted photographing order information is read out from the storage apparatus 26. The extracted photographing order information is transmitted through the communication terminal 10-1 to the portable terminal 10 to be transmitted (step S57) and the second radiograph preparation processing is finished.

The operator for operating the control apparatus 20 can easily prepare the cassette necessary for the photography on the basis of the photographing order information which is in the portable terminal 10 to be extracted and which is displayed on the display unit 23 by the execution of the second radiograph preparation processing.

Further, as well as the second radiograph pre-processing of FIG. 16, the portable terminal 10 to be extracted receives the extracted photographing order information through the communication terminal 10-1, stores it in the storage apparatus 26, and displays it on the display unit 13.

The operator for operating the control apparatus 20 can reconfirm the cassette 50 prepared on the basis of the photographing order information displayed on the display unit 23 with reference to the extracted photographing order information displayed on the display unit 13 of the portable terminal 10.

According to the embodiment, because of computing and displaying in the control apparatus 20 the photographing order information extracted on the basis of the extract condition which is in each portable terminal 10 and which is required by the operator, and the size and the number of cassette necessary for the photography, the operator can easily and reliably prepare the cassette without any other works by referring to the size and the number of cassette corresponding to the extract condition.

Further, because the photographing order information including the size and the number of cassette is displayed on each portable terminal 10, the operator can refer to and reconfirm the size and the number of cassette corresponding to the extract condition. Thereby, the operator can easily and reliably carry out the photography with reference to the photographing order information corresponding to the extract condition, which makes more effective the photography.

Further, the above described each embodiment is an example of the medical image photographing system and the medical image managing method preferable for the present invention, and is not limited thereto.

For example, the system structure of the above described medical image photographing system 100 is an example, and is not limited thereto. Like the medical image photographing system 200 shown in FIG. 18, the communication terminal 10-1 for controlling the communication between the portable terminal 10 and the control apparatus 20 may not be connected direct to the control apparatus 20, and may be connected to the network N and communicate predetermined control apparatuses 20 through the network N.

In the medical image photographing system 200, the photographing order information can be transmitted from a plurality of control apparatuses 20 to one portable terminal 10. By applying the above described second embodiment to the medical image photographing system 200, in each control apparatus 20, the photographing order information corresponding to the extract condition may be extracted from all photographing order information corresponding to the predetermined portable terminal 10 on the basis of the photographing order information to be transmitted from the information management apparatus 60.

Further, in the above described each embodiment, although the size and the number of cassette are computed in the portable terminal 10, the photographing order information to be transmitted from the information management apparatus 60 to the control apparatus 20 may previously include the size and the number of cassette.

Further, the photographing order information (and the size and the number of cassette) may be displayed on one of the portable terminal 10 and the control apparatus 20. When it comes to the portable radiography, it may be determined whether the portable terminal 10 or the control apparatus 20 computes (extracts) the photographing order information, the size and the number of cassette, and displays the photographing order information, the size and the number of cassette, by considering the workflow of the operator, whereby the computing (extracting) unit (such as, by each patient to be photographed, by each portable terminal (respectively corresponding to patients), and by each operator) may be determined.

Further, in the above described embodiment, although the photographing order information and the additional information, that is, the size and the number of cassette may be displayed on the portable terminal 10, it is not limited thereto. For example, if the photography positioning information is included in the photographing order information, the information such as the doctor's round (photographing) route and the position of the patient bed may be displayed as the additional information. Further, the first display unit for displaying the photographing order information, its size and number of cassette, and the second display unit for displaying the doctor's round route may be disposed on the portable terminal 10. For example, the first display unit and the second display unit may be respectively disposed on the surface of the portable terminal 10 and the backside thereof.

Further, in the above described each embodiment, although the size and the number of cassette are computed after the photographing order information is extracted in the radiograph pre-processing, the size and the number of cassette that are not extracted may be previously computed before the size and the number of cassette are selected for the extract condition.

Further, the photographing order information to be transmitted from the control apparatus 20 to the portable terminal 10 may include the place (for example, IP address for identifying the computer on the network) to which the cassette ID corresponded to the photographing order information with its photography finished is transmitted.

Further, although the operator ID, the cassette ID, and the radiographing apparatus ID are obtained by the barcode reader 17 of the portable terminal 10, it is not limited thereto. The ID card of the operator, the cassette 50, and the portable radiographing apparatus 40 may have IC chip recording each identification information. The identification information recorded in IC chip may be obtained by the portable terminal 10. In this case, the portable terminal 10 has IC reader (not shown).

Further, the information stored in the photograph history management file 261 is not limited thereto, and can store various information. For example, the photograph history management file 261 may store the photographing order information. Considering other information relating to the photography, the identification number of the portable terminal 10, the identification number of the communication terminal 10-1, the image processing condition on image processing, and the operator ID who carried out the image processing may be corresponded to the photographing order information and stored in the photograph history management file 261. Further, corresponding the photographing order information thereto may be carried out on the basis of various information such as the photographing ID, the cassette ID, and the patient ID. Further, the corresponding relation between the photographing order information and the medical image may be cleared on the basis of various information as well.

Further, the timing that the operator ID, the cassette ID, and the photographing ID are obtained is not limited to the above described example, and can be changed to the predetermined timing if the corresponding relation to the photographing order information is clear. For example, in the radiograph pre-processing, the operator ID may be included in the photographing order information to be transmitted from the control apparatus 20 to the portable terminal 10. In this case, in the radiograph start processing, only the operator ID may be identified in the portable terminal 10. Otherwise, if the cassette ID is obtained after the photography finished, the cassette ID may not be obtained before the photography starts.

It will however, be evident that various changes may be made thereto without departing from the broader scope of the present invention, for each structure, its details and operations of the medical image photographing apparatus 100 and 200 of the above described embodiment The entire disclosure of Japanese Patent Application No. Tokugan 2003-91042 filed on Mar. 28, 2003 is incorporated herein by reference in its entirety.

What is claimed is:

1. A medical image photographing system comprising a control apparatus for corresponding a photographing order information related to medical photography and a medical image and managing them, and a portable terminal for obtaining the photographing order information from the control apparatus;

wherein the control apparatus comprises a first communication unit for communicating with the portable terminal, and a first control unit for transmitting the photographing order information through the first communication unit to the portable terminal;

wherein the portable terminal comprises a second communication unit for communicating with the control apparatus, a display unit for displaying display information, and a second control unit for receiving the photographing order information from the control apparatus through the second communication unit, extracting the photographing order information corresponding to a predetermined extract condition from the received photographing order information, and displaying the extracted photographing order information on the display unit; and wherein the second control unit computes an additional information having one of or both of a size and a number of a photograph from the photographing order information to be extracted, and displays the additional information and the photographing order information on the display unit.

2. A medical image managing method for a medical image photographing system comprising a control apparatus for corresponding a photographing order information related to medical photography and a medical image and managing them, and a portable terminal for obtaining the photographing order information from the control apparatus, the method comprising:

transmitting the photographing order information to the portable terminal in the control apparatus;

receiving the photographing order information from the control apparatus, extracting the photographing order information corresponding to a predetermined extract condition from the received photographing order information, and displaying the extracted photographing order information in the portable terminal; and computing an additional information having one of or both of a size and a number of a photograph necessary for imaging from the photographing order information to be extracted and displaying the additional information and the photographing order information in the portable terminal.

3. A medical image managing method for a medical image photographing system comprising a control apparatus for corresponding a photographing order information related to medical photography and a medical image and managing them, and a portable terminal for obtaining the photographing order information from the control apparatus, the method comprising:

extracting the photographing order information corresponding to a predetermined extract condition from the photographing order information and displaying the extracted photographing order information in the control apparatus; and computing an additional information having one of or both of a size and a number of a photograph necessary for imaging from the photographing order information to be extracted, and displaying the additional information and the extracted photographing order information in the control apparatus.

4. The method of claim 3, further comprising:

transmitting the extracted photographing order information to the portable terminal in the control apparatus, receiving the extracted photographing order information from the control apparatus, and displaying the extracted photographing order information in the portable terminal.

* * * * *